(12) United States Patent
Popp et al.

(10) Patent No.: US 9,629,757 B2
(45) Date of Patent: Apr. 25, 2017

(54) ABSORBENT ARTICLE INCLUDING CONTAINMENT FLAPS

(71) Applicant: Kimberly-Clark Worldwide, Inc., Neenah, WI (US)

(72) Inventors: Robert Lee Popp, Greenville, WI (US); Julie Ann Paveletzke, Appleton, WI (US); Michael John Faulks, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 751 days.

(21) Appl. No.: 13/900,211

(22) Filed: May 22, 2013

(65) Prior Publication Data

US 2014/0350508 A1 Nov. 27, 2014

(51) Int. Cl.
| | | |
|---|---|---|
| A61F 13/15 | (2006.01) | |
| A61F 13/494 | (2006.01) | |
| A61F 13/49 | (2006.01) | |
| A61F 13/47 | (2006.01) | |
| A61F 13/475 | (2006.01) | |

(52) U.S. Cl.
CPC .. *A61F 13/49406* (2013.01); *A61F 13/49001* (2013.01); *A61F 13/4942* (2013.01); *A61F 13/49413* (2013.01); *A61F 13/15747* (2013.01); *A61F 13/4704* (2013.01); *A61F 13/475* (2013.01); *A61F 13/4752* (2013.01); *A61F 13/4753* (2013.01); *A61F 13/4757* (2013.01)

(58) Field of Classification Search
CPC ............ A61F 13/15747; A61F 13/4704; A61F 13/475; A61F 13/4751; A61F 13/4752; A61F 13/4753; A61F 13/4757

USPC .......... 604/385.28, 385.201, 385.24, 385.25, 604/385.27, 385.29
See application file for complete search history.

(56) References Cited

U.S. PATENT DOCUMENTS

| | | |
|---|---|---|
| 4,704,116 A | 11/1987 | Enloe |
| 5,567,254 A | 10/1996 | Sageser |
| 5,582,606 A | 12/1996 | Bruemmer et al. |
| 5,624,426 A | 4/1997 | Roe et al. |
| 5,674,215 A | 10/1997 | Roennberg |
| 5,906,603 A | 5/1999 | Roe et al. |
| 6,050,984 A | 4/2000 | Fujioka et al. |
| 6,156,023 A | 12/2000 | Yoshioka |

(Continued)

FOREIGN PATENT DOCUMENTS

| | | |
|---|---|---|
| EP | 0 677 284 B1 | 6/1999 |
| EP | 0 938 437 B1 | 1/2001 |

(Continued)

*Primary Examiner* — Jacqueline Stephens

(57) ABSTRACT

An absorbent article having a first and a second containment flap each having a stem, an inner flap projection, and an outer flap projection. The absorbent article can include a first and a second folding line for packaging each being substantially parallel to the longitudinal axis. The first and second containment flaps can be positioned in the absorbent article such that the distal end of the outer flap projections can be positioned laterally inside of each folding line, the distal ends of the inner flap projections can be positioned laterally outside of each folding line, or such that the first fold line extends through at least a portion of the inner or the outer flap projection of the first containment flap and the second fold line extends through at least a portion of the inner or the outer flap projection of the second containment flap.

26 Claims, 18 Drawing Sheets

(56) References Cited

U.S. PATENT DOCUMENTS

| | | |
|---|---|---|
| 6,159,191 A | 12/2000 | Mishima et al. |
| 6,682,515 B1 | 1/2004 | Mizutani et al. |
| 6,706,029 B1 | 3/2004 | Suzuki et al. |
| 6,786,895 B1 | 9/2004 | Schmitz et al. |
| 7,014,632 B2 | 3/2006 | Takino et al. |
| 7,048,726 B2 | 5/2006 | Kusagawa et al. |
| 7,435,243 B2 | 10/2008 | Miyamoto |
| 7,435,309 B2 | 10/2008 | Komatsu |
| 7,507,224 B2 | 3/2009 | Datta et al. |
| 7,527,616 B2 | 5/2009 | Miyamoto |
| 7,641,642 B2 | 1/2010 | Murai et al. |
| 7,744,578 B2 | 6/2010 | Tanio et al. |
| 7,879,017 B1 | 2/2011 | Tabata et al. |
| 7,918,839 B2 | 4/2011 | Ehrnsperger et al. |
| 7,922,706 B2 | 4/2011 | Konawa |
| 8,062,279 B2 | 11/2011 | Miyamoto |
| 8,075,543 B2 | 12/2011 | Okuda |
| 2002/0052591 A1 | 5/2002 | Zehner et al. |
| 2002/0128626 A1 | 9/2002 | Friderich et al. |
| 2005/0049568 A1 | 3/2005 | Underhill et al. |
| 2005/0124961 A1 | 6/2005 | Morman et al. |
| 2005/0222550 A1 | 10/2005 | Mitsui et al. |
| 2005/0222553 A1 | 10/2005 | Crislip |
| 2007/0213678 A1 | 9/2007 | Thorson et al. |
| 2008/0021426 A1 | 1/2008 | Nakagawa et al. |
| 2009/0312730 A1 | 12/2009 | Lavon et al. |
| 2009/0312737 A1 | 12/2009 | LaVon et al. |
| 2010/0228219 A1 | 9/2010 | Carlson et al. |
| 2011/0046596 A1 | 2/2011 | Kudo et al. |
| 2011/0288519 A1 | 11/2011 | Miyamoto |
| 2012/0277713 A1 | 11/2012 | Raycheck et al. |
| 2012/0304363 A1 | 12/2012 | Sablone |

FOREIGN PATENT DOCUMENTS

| | | |
|---|---|---|
| EP | 1 133 963 A2 | 9/2001 |
| JP | 02-274250 A | 11/1990 |
| JP | 2824859 B2 | 11/1998 |
| JP | 2001-293029 A | 10/2001 |
| JP | 2002-177324 A | 6/2002 |
| JP | 3737399 B2 | 1/2006 |
| JP | 2006-247272 A | 9/2006 |
| JP | 2007-185270 A | 7/2007 |
| JP | 4959436 B2 | 6/2012 |
| WO | WO 2011/162069 A1 | 12/2011 |

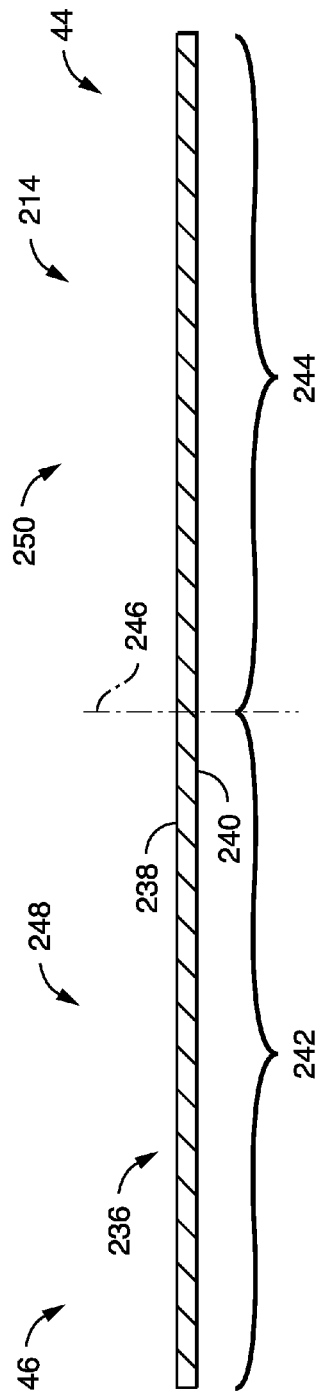
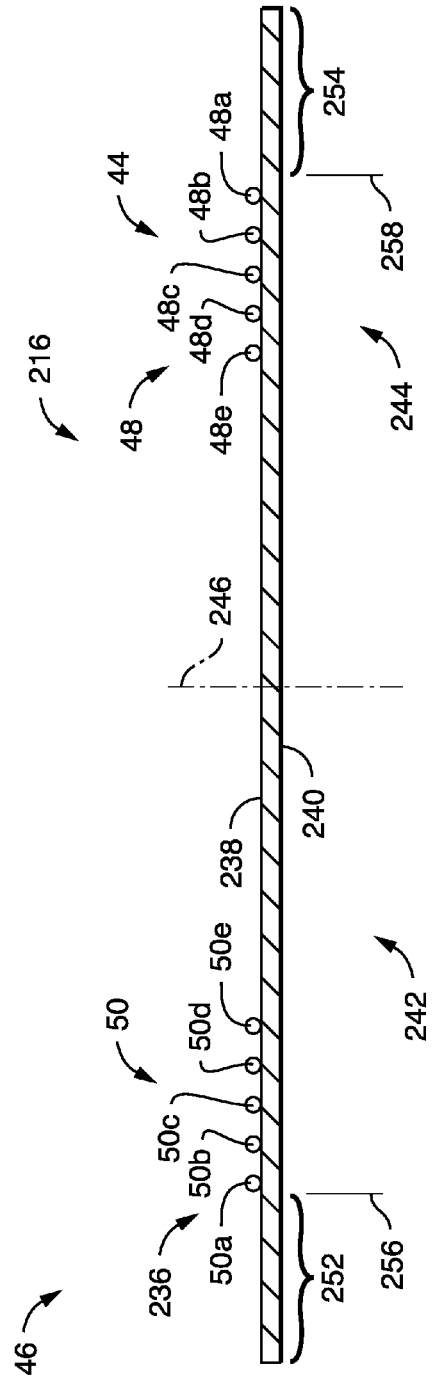
FIG. 8
FIG. 9

ABSORBENT ARTICLE INCLUDING CONTAINMENT FLAPS

BACKGROUND

One of the primary functions of personal care absorbent articles is to retain and absorb body exudates such as urine, fecal material, blood, and menses. Along these lines, a desired attribute of personal care absorbent articles is to minimize the leakage of such exudates from the absorbent article. To assist in achieving this function, absorbent articles can include leg containment flaps in the crotch region of the absorbent article. These containment flaps can be designed to provide a gasket, or seal, against a wearer's skin to prevent leakage of the exudates from the absorbent article, as well as to contain the exudates in a specific area of the absorbent article such that the exudates can be properly distributed, further contained, and/or absorbed by various components of the absorbent article.

Various configurations of containment flaps and methods of forming containment flaps are known. For example, one common configuration is to have a containment flap on each side of the longitudinal axis of the absorbent article by providing a length of material with one or more elastic strands contained in the material, the length of material extending substantially along the length of the absorbent article. The elastic strand(s) can adhere to the strip of material to gather each containment flap in the crotch region of the absorbent article when the absorbent article is in a relaxed condition such that the material stands up or extends away from the absorbent article. The top edge of each vertical containment flap is configured to contact the wearer's skin along the length of the containment flap to form a seal against exudates. However, the limited area of contact between the top edge of each vertical containment flap along the wearer's skin can provide less than desirable gasketing properties in some circumstances While other configurations of containment flaps are known that increase the area of contact with the wearer's skin, many have only been theorized and present manufacturing complexities and/or packaging drawbacks not initially realized. As an example, other containment flap systems for absorbent articles that provide increased contact area with the wearer's skin do not address packaging concerns such as fold lines in the absorbent article and the interactions of such fold lines with the functioning of the containment flaps to contain body exudates. These prior containment flap system also do not address how to use packaging fold lines as a way to selectively alter the shape of the containment flaps to provide further gasketing benefits with the wearer's skin.

Thus, there is a need for an absorbent article having containment flaps which can provide an improved gasket with the wearer's skin, yet still provide reduced irritation on the wearer's skin. There is also a need for a method of producing such containment flaps. Additionally, there is a need for an absorbent article can be packaged with fold lines that are selectively positioned so as to fully utilize the performance characteristics of the containment flaps and/or to selectively alter the shape of a portion of the containment flaps to provide enhanced gasketing properties with the wearer's skin.

SUMMARY

In one embodiment, an absorbent article can include a longitudinal axis and a lateral axis, a front end region, a rear end region, and a crotch region. The crotch region can be disposed between the front end region and the rear end region. The absorbent article can further include a front end edge in the front end region, a rear end edge in the rear end region, and a first longitudinal side edge and a second longitudinal side edge. The first longitudinal side edge and the second longitudinal side edge can each extend from the front end edge to the rear end edge. The absorbent article can also include a body facing liner comprising a body facing surface and a garment facing surface, a backsheet coupled to the body facing liner, and an absorbent body positioned between the body facing liner and the backsheet. The absorbent article can additionally include a first containment flap and a second containment flap. The first containment flap and the second containment flap can each extend from the front end region to the rear end region. The first containment flap can be on a first side of the longitudinal axis and the second containment flap can be on a second side of the longitudinal axis. The first containment flap and the second containment flap can each include a stem, an inner flap projection, and an outer flap projection. The stem can be bonded to one of the body facing liner and the backsheet. The stem can be configured to extend away from the body facing surface of the body facing liner and the backsheet in at least the crotch region when the absorbent article is in a relaxed condition. The inner flap projection can extend laterally from the stem towards the longitudinal axis when the absorbent article is in the relaxed condition. At least a portion of the inner flap projection can be elasticized. The outer flap projection can extend laterally from the stem away from the longitudinal axis and the inner flap projection to a distal end when the absorbent article is in the relaxed condition. At least a portion of the outer flap projection can be elasticized. The absorbent article can further include a first fold line for packaging that can be substantially parallel to the longitudinal axis on the first side of the longitudinal axis. The first fold line can extend from the front end edge to the rear end edge. The absorbent article can further include a second fold line for packaging that can be substantially parallel to the longitudinal axis on the second side of the longitudinal axis and that can extend from the front end edge to the rear end edge. The distal end of the outer flap projection of the first containment flap can be positioned laterally inside of the first folding line when the absorbent article is in an unfolded and stretched condition.

In another embodiment, an absorbent article can include a longitudinal axis and a lateral axis, a front end region, a rear end region, and a crotch region. The crotch region can be disposed between the front end region and the rear end region. The absorbent article can further include a front end edge in the front end region, a rear end edge in the rear end region, and a first longitudinal side edge and a second longitudinal side edge. The first longitudinal side edge and the second longitudinal side edge can each extend from the front end edge to the rear end edge. The absorbent article can also include a body facing liner comprising a body facing surface and a garment facing surface, a backsheet coupled to the body facing liner, and an absorbent body positioned between the body facing liner and the backsheet. The absorbent article can additionally include a first containment flap and a second containment flap. The first containment flap and the second containment flap can each extend from the front end region to the rear end region. The first containment flap can be on a first side of the longitudinal axis and the second containment flap can be on a second side of the longitudinal axis. The first containment flap and the second containment flap can each include a stem, an inner flap projection, and an outer flap projection. The stem can be bonded to one of the body facing liner and the backsheet. The stem can be configured to extend away from the body facing surface of the body facing liner and the backsheet in at least the crotch region when the absorbent article is in a relaxed condition. The stem of the first containment flap being can be positioned laterally inward of the first longitudinal side edge and the stem of the second containment flap can be positioned laterally inward of the second longitudinal side edge. The inner flap projection can extend laterally from the stem towards the longitudinal axis to a distal end when the absorbent article is in the relaxed condition. At least a portion of the inner flap projection can be elasticized. The outer flap projection can extend laterally from the stem away from the longitudinal axis and the inner flap projection when the absorbent article is in the relaxed condition. At least a portion of the outer flap projection can be elasticized. The absorbent article can further include a first fold line for packaging that can be substantially parallel to the longitudinal axis on the first side of the longitudinal axis. The first fold line can extend from the front end edge to the rear end edge. The absorbent article can further include a second fold line for packaging that can be substantially parallel to the longitudinal axis on the second side of the longitudinal axis and that can extend from the front end edge to the rear end edge. The distal end of the inner flap projection of the first containment flap can be positioned laterally outside of the first folding line when the absorbent article is in an unfolded and stretched condition.

In yet another embodiment, an absorbent article can include a longitudinal axis and a lateral axis, a front end region, a rear end region, and a crotch region. The crotch region can be disposed between the front end region and the rear end region. The absorbent article can further include a front end edge in the front end region, a rear end edge in the rear end region, and a first longitudinal side edge and a second longitudinal side edge. The first longitudinal side edge and the second longitudinal side edge can each extend from the front end edge to the rear end edge. The absorbent article can also include a body facing liner comprising a body facing surface and a garment facing surface, a backsheet coupled to the body facing liner, and an absorbent body positioned between the body facing liner and the backsheet. The absorbent article can additionally include a first containment flap and a second containment flap. The first containment flap and the second containment flap can each extend from the front end region to the rear end region. The first containment flap can be on a first side of the longitudinal axis and the second containment flap can be on a second side of the longitudinal axis. The first containment flap and the second containment flap can each include a stem, an inner flap projection, and an outer flap projection. The stem can be bonded to one of the body facing liner and the backsheet. The stem can be configured to extend away from the body facing surface of the body facing liner and the backsheet in at least the crotch region when the absorbent article is in a relaxed condition. The stem can extend substantially parallel to the body facing surface of the body facing liner and the backsheet when the absorbent article is in a stretched condition. The inner flap projection can extend laterally from the stem towards the longitudinal axis when the absorbent article is in the relaxed condition and can extend substantially parallel to the stem towards the longitudinal axis when the absorbent article is in the stretched condition. At least a portion of the inner flap projection can be elasticized. The outer flap projection can extend laterally from the stem away from the longitudinal axis and the inner flap projection when the absorbent article is in the relaxed condition and can substantially parallel to the stem and away from the longitudinal axis when the absorbent article is in the stretched condition. At least a portion of the outer flap projection can be elasticized. The absorbent article can further include a first fold line for packaging a first that can be substantially parallel to the longitudinal axis and be on the first side of the longitudinal axis. The first fold line can extend from the front end edge to the rear end edge. The first fold line can extend through at least a portion of the first containment flap including through at least one of the inner flap projection of the first containment flap and the outer flap projection of the first containment flap when the absorbent article is in an unfolded and stretched condition. The absorbent article can further include a second fold line for packaging that can be substantially parallel to the longitudinal axis and be on the second side of the longitudinal axis. The second fold line can extend from the front end edge to the rear end edge.

BRIEF DESCRIPTION OF THE DRAWINGS

A full and enabling disclosure thereof, directed to one of ordinary skill in the art, is set forth more particularly in the remainder of the specification, which makes reference to the appended figures in which:

FIG. 8 is a cross-section view of a step of the method shown in FIG. 7.

FIG. 9 is a cross-section view of a step of the method shown in FIG. 7.

DETAILED DESCRIPTION

Figure 1:
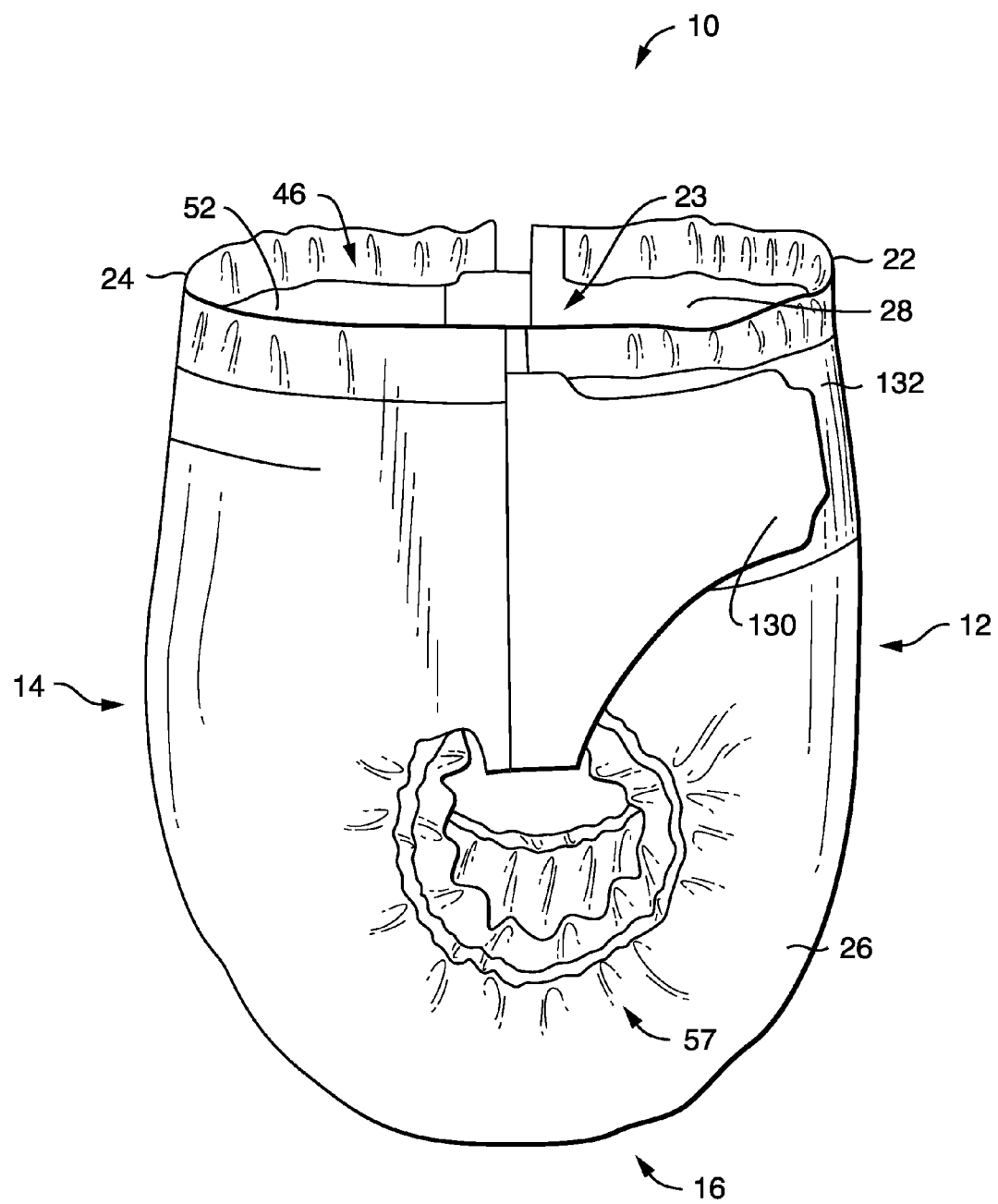
FIG. 1 is a side perspective view of an exemplary embodiment of an absorbent article, such as a diaper, in a fastened condition.

In an embodiment, the present disclosure is generally directed towards an absorbent article that can have containment flaps that provide an improved gasket with the wearer's skin as well as an exemplary method for producing an absorbent article including such containment flaps. Each example is provided by way of explanation and is not meant as a limitation. For example, features illustrated or described as part of one embodiment or figure can be used on another embodiment or figure to yield yet another embodiment. It is intended that the present disclosure include such modifications and variations.

DEFINITIONS

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements. The bonding of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" refers herein to one who fits an absorbent article, such as, but not limited to, a diaper, training pant, youth pant, incontinent product, or other absorbent article about the wearer of one of these absorbent articles. A user and a wearer can be one and the same person.

Figure 2:
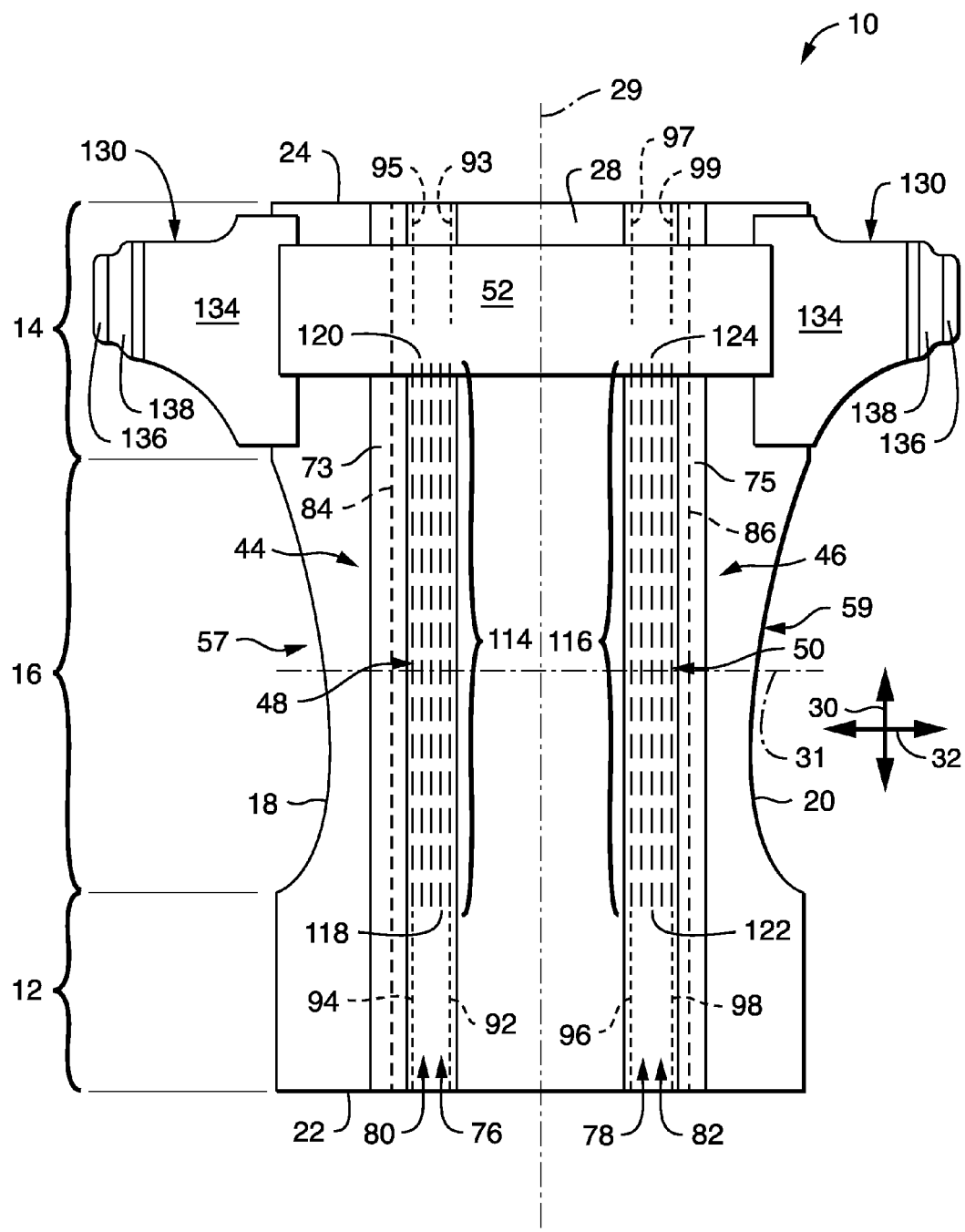
FIG. 2 is a top plan view of the absorbent article of FIG. 1, in an unfastened, stretched, and laid flat condition with the body facing surface of the absorbent article which contacts the wearer facing the viewer.

Absorbent Article:

Referring to FIGS. 1 and 2, a non-limiting illustration of an absorbent article 10, for example, a diaper, is illustrated. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure. The absorbent article 10 illustrated in FIGS. 1 and 2 includes a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region. The absorbent article 10 has a pair of longitudinal side edges, 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The absorbent article 10 can have a longitudinal axis 29 and a lateral axis 31.

The absorbent article 10 can include a backsheet 26 and a body facing liner 28. In an embodiment, the body facing liner 28 can be bonded to the backsheet 26 in a superposed relation by any suitable means such as, but not limited to, adhesives, ultrasonic bonds, thermal bonds, pressure bonds, or other conventional techniques. The backsheet 26 can define a length in a longitudinal direction 30, and a width in the lateral direction 32, which, in the illustrated embodiment, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32.

Figure 3:
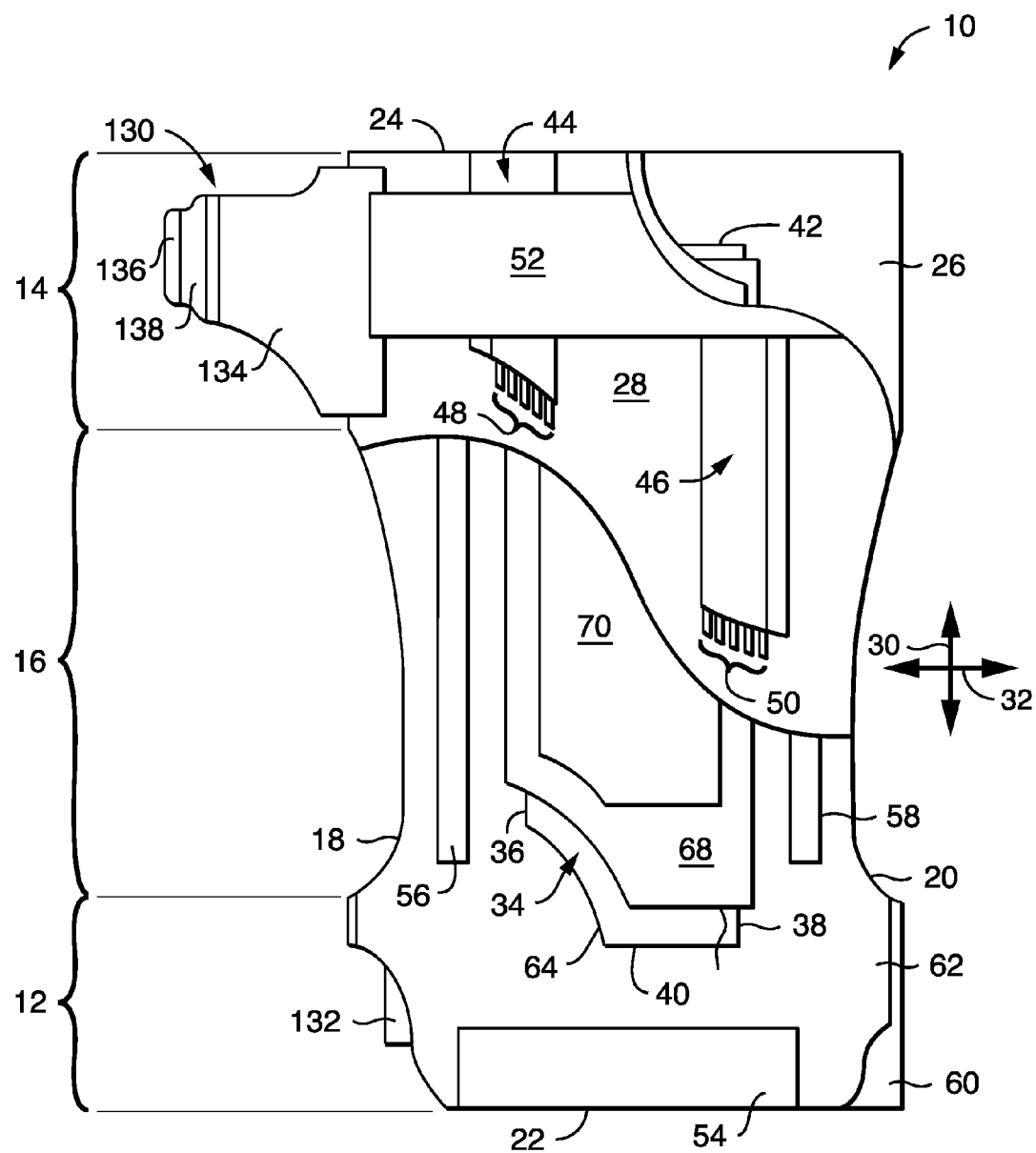
FIG. 3 is a top plan view of the absorbent article of FIG. 1, with portions cut away for clarity of illustration.

FIG. 3 illustrates the absorbent article 10 with certain portions cut-away for illustrating additional aspects of the absorbent article 10. An absorbent body 34 can be disposed between the backsheet 26 and the body facing liner 28. The absorbent body 34 can have longitudinal edges, 36 and 38, which, in an embodiment, can form portions of the longitudinal side edges, 18 and 20, respectively, of the absorbent article 10 and can have opposite end edges, 40 and 42, which, in an embodiment, can form portions of the waist edges, 22 and 24, respectively, of the absorbent article 10. In an embodiment, the absorbent body 34 can have a length and width that are the same as or less than the length and width of the absorbent article 10.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening 23. Portions of the longitudinal side edges, 18 and 20, in the crotch region 16 can generally define leg openings when the absorbent article 10 is worn.

The absorbent article 10 can be configured to contain and/or absorb liquid, solid, and semi-solid body exudates discharged from the wearer. For example, containment flaps, 44 and 46, can be configured to provide a barrier to the lateral flow of body exudates. As illustrated in FIG. 3, each containment flap 44, 46 can include an elastic member 48, 50. The elastic members 48, 50 can include one or more elastic strands (five are shown in FIG. 3) that are aligned substantially parallel to the longitudinal axis 29 of the absorbent article 10. The containment flaps 44, 46 are laterally spaced from one another, such that the containment flap 44 is on one side of the longitudinal axis 29 and the containment flap 46 is on an opposite side of the longitudinal axis 29. The containment flaps 44, 46 can be attached to the absorbent article by being bonded to the body facing liner 28, as will be further discussed below. The containment flaps, 44 and 46, can be located laterally inward from the longitudinal side edges, 18, 20 of the absorbent article 10, and can extend longitudinally along the entire length of absorbent article 10 or can extend partially along the length of the absorbent article 10.

To further enhance containment and/or absorption of body exudates, the absorbent article 10 can suitably include a rear waist elastic member 52, a front waist elastic member 54, and leg elastic members, 56 and 58, as are known to those skilled in the art. The waist elastic members, 52 and 54, can be attached to the backsheet 26 and/or the body facing liner 28 along the opposite waist edges, 22 and 24, and can extend over part or all of the waist edges, 22 and 24. In an embodiment shown in FIG. 3, the rear waist elastic member 52 is attached to the body facing liner 28 and the containment flaps 44, 46 and the front waist elastic member 54 is attached to the backsheet 26. The leg elastic members, 56 and 58, can be attached to the backsheet 26 and/or the body facing liner 28 along the opposite longitudinal side edges, 18 and 20, and positioned in the crotch region 16 of the absorbent article 10.

Additional details regarding each of these elements of the absorbent article 10 described herein can be found below and with reference to the FIGS. 1 through 13.

Backsheet:

The backsheet 26 and/or portions thereof can be breathable and/or liquid impermeable. The backsheet 26 and/or portions thereof can be elastic, stretchable, or non-stretchable. The backsheet 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the backsheet 26 can be constructed of a microporous polymeric film, such as polyethylene or polypropylene.

In an embodiment, the backsheet 26 can be a single layer of a liquid impermeable material. In an embodiment, the backsheet 26 can be suitably stretchable, and more suitably elastic, in at least the lateral or circumferential direction 32 of the absorbent article 10. In an embodiment, the backsheet 26 can be stretchable, and more suitably elastic, in both the lateral 32 and the longitudinal 30 directions. In an embodiment, the backsheet 26 can be a multi-layered laminate in which at least one of the layers is liquid impermeable. In an embodiment, the backsheet 26 can be a two layer construction, including an outer layer 60 material and an inner layer 62 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 62 can be bonded to the outer layer 60 by other bonding methods, including, but not limited to, ultrasonic bonds, thermal bonds, pressure bonds, or the like.

The outer layer 60 of the backsheet 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 60 of a backsheet 26 can be a 20 gsm spunbond polypropylene non-woven web. The outer layer 60 may also be constructed of the same materials from which the body facing liner 28 can be constructed as described herein.

The liquid impermeable inner layer 62 of the backsheet 26 (or the liquid impermeable backsheet 26 where the backsheet 26 is of a single-layer construction) can be either vapor permeable (i.e., "breathable") or vapor impermeable. The liquid impermeable inner layer 62 (or the liquid impermeable backsheet 26 where the backsheet 26 is of a single-layer construction) may be manufactured from a thin plastic film, although other liquid impermeable materials may also be used. The liquid impermeable inner layer 62 (or the liquid impermeable backsheet 26 where the backsheet 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 62 (or the liquid impermeable backsheet 26 where the backsheet 26 is of a single-layer construction) can be a printed 19 gsm Berry Plastics XP-8695H film or equivalent commercially available from Berry Plastics Corporation, Evansville, Ind., U.S.A.

Where the backsheet 26 is of a single layer construction, it can be embossed and/or matte finished to provide a more cloth-like texture or appearance. The backsheet 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer and the liquid loading imparted by the intended use of the absorbent article 10. Additionally, the size and the absorbent capacity of the absorbent body 34 can be varied to accommodate wearers ranging from infants to adults.

The absorbent body 34 may have a length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 34 may have a crotch region 16 width ranging from about 30, 40, 50, 55, 60, 65, or 70 mm to about 75, 80, 85, 90, 95, 100, 105, 110, 115, 120, 125, 130, 140, 150, 160, 170 or 180 mm. The width of the absorbent body 34 located within the front waist region 12 and/or the back waist region 14 of the absorbent article 10 may range from about 50, 55, 60, 65, 70, 75, 80, 85, 90, or 95 mm to about 100, 105, 110, 115, 120, 125 or 130 mm. As noted herein, the absorbent body 34 can have a length and width that can be less than or equal to the length and width of the absorbent article 10.

In an embodiment, the absorbent article 10 can be a diaper having the following ranges of lengths and widths of an absorbent body 34 having an hourglass shape: the length of the absorbent body 34 may range from about 170, 180, 190, 200, 210, 220, 225, 240 or 250 mm to about 260, 280, 300, 310, 320, 330, 340, 350, 355, 360, 380, 385, or 390 mm; the width of the absorbent body 34 in the crotch region 16 may range from about 40, 50, 55, or 60 mm to about 65, 70, 75, or 80 mm; the width of the absorbent body 34 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 34 having an hourglass shape: the length of the absorbent body 34 may range from about 400, 410, 420, 440 or 450 mm to about 460, 480, 500, 510 or 520 mm; the width of the absorbent body 34 in the crotch region 16 may range from about 50, 55, or 60 mm to about 65, 70, 75, or 80 mm; the width of the absorbent body 34 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 34 having a rectangular shape: the length of the absorbent body 34 may range from about 400, 410 or 415 to about 425 or 450 mm; the width of the absorbent body 34 in the crotch region 16 may range from about 90, or 95 mm to about 100, 105, or 110 mm. It should be noted that the absorbent body 34 of an adult incontinence garment may or may not extend into either or both the front waist region 12 or the back waist region 14 of the absorbent article 10.

The absorbent body 34 can have two surfaces such as a wearer facing surface 64 and a garment facing surface 66. Edges, such as longitudinal side edges, 36 and 38, and such as front and back end edges, 40 and 42, can connect the two surfaces, 64 and 66.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material.

In an embodiment, the absorbent body 34 may be constructed of a single layer of materials, or in the alternative, may be constructed of two or more layers of materials. In an embodiment in which the absorbent body 34 has two layers, the absorbent body 34 can have a wearer facing layer suitably composed of hydrophilic fibers and a garment facing layer suitably composed at least in part of a high absorbency material commonly known as superabsorbent material. In such an embodiment, the wearer facing layer of the absorbent body 34 can be suitably composed of cellulosic fluff, such as wood pulp fluff, and the garment facing layer of the absorbent body 34 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that, in an embodiment, the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 34 with a lower absorbent capacity in the wearer facing layer than in the garment facing layer.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff. An example of wood pulp fluff can be "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

The absorbent body 34 can be formed with a dry-forming technique, an air-forming technique, a wet-forming technique, a foam-forming technique, or the like, as well as combinations thereof. A coform nonwoven material may also be employed. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 34.

In an embodiment, the absorbent body 34 can be free of superabsorbent material. In an embodiment, the absorbent body 34 can have at least about 15% by weight of a superabsorbent material. In an embodiment, the absorbent body 34 can have at least about 15, 20, 25, 30, 35, 40, 45, 50, 55, 60, 65, 70, 75, 80, 85, 90, 95, 99 or 100% by weight of a superabsorbent material. In an embodiment, the absorbent body 34 can have less than about 100, 99, 95, 90, 85, 80, 75, 70, 65, 60, 55, 50, 45, 40, 35, 30, 25, or 20% by weight of a superabsorbent material. In an embodiment, the absorbent body 34 can have from about 15, 20, 25, 30, 35, 40, 45, 50, 55 or 60% to about 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 34 can be superposed over the inner layer 62 of the backsheet 26, extending laterally between the leg elastic members, 56, 58, and can be bonded to the inner layer 62 of the backsheet 26, such as by being bonded thereto with adhesive. However, it is to be understood that the absorbent body 34 may be in contact with, and not bonded with, the backsheet 26 and remain within the scope of this disclosure. In an embodiment, the backsheet 26 can be composed of a single layer and the absorbent body 34 can be in contact with the singer layer of the backsheet 26. In an embodiment, a layer, such as but not limited to, a fluid transfer layer 68, can be positioned between the absorbent body 40 and the backsheet 26.

Fluid Transfer Layer:

In various embodiments an absorbent article 10 can be constructed without a fluid transfer layer 68. In various embodiments the absorbent article 10 can have a fluid transfer layer 68. In an embodiment, the fluid transfer layer 68 can be in contact with the absorbent body 34. In an embodiment, the fluid transfer layer 68 can be bonded to the absorbent body 34. Bonding of the fluid transfer layer 68 to the absorbent body 34 can occur via any means known to one of ordinary skill, such as, but not limited to, adhesives. In an embodiment, a fluid transfer layer 68 can be positioned between the body facing liner 28 and the absorbent body 34. In an embodiment, a fluid transfer layer 68 can completely encompass the absorbent body 34 and can be sealed to itself. In such an embodiment, the fluid transfer layer 68 may be folded over on itself and then sealed using, for example, heat and/or pressure. In an embodiment a fluid transfer layer 68 may be composed of separate sheets of material which can be utilized to partially or fully encompass the absorbent body 34 and which can be sealed together using a sealing means such as, but not limited to, an ultrasonic bonder or other thermochemical bonding means or the use of an adhesive.

In an embodiment, the fluid transfer layer 68 can be in contact with and/or bonded with the wearer facing surface 64 of the absorbent body 34. In an embodiment, the fluid transfer layer 68 can be in contact with and/or bonded with the wearer facing surface and at least one of the edges, 36, 38, 40, and/or 42, of the absorbent body 34. In an embodiment, the fluid transfer layer 68 can be in contact with and/or bonded with the wearer facing surface 64, at least one of the edges, 36, 38, 40, and/or 42, and the garment facing surface 66 of the absorbent body 34. In an embodiment, the absorbent body 34 may be partially or completely encompassed by a fluid transfer layer 68.

The fluid transfer layer 68 can be pliable, less hydrophilic than the absorbent body 34, and sufficiently porous to thereby permit liquid body exudates to penetrate through the fluid transfer layer 68 to reach the absorbent body 34. In an embodiment, the fluid transfer layer 68 can have sufficient structural integrity to withstand wetting thereof and of the absorbent body 34. In an embodiment, the fluid transfer layer 68 can be constructed from a single layer of material or it may be a laminate constructed from two or more layers of material.

In an embodiment, the fluid transfer layer 68 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp. Wood pulps can include, but are not limited to, standard softwood fluffing grade such as "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

In various embodiments, the fluid transfer layer 68 can include cellulosic material. In various embodiments, the fluid transfer layer 68 can be creped wadding or a high-strength tissue. In various embodiments, the fluid transfer layer 68 can include polymeric material. In an embodiment, a fluid transfer layer 68 can include a spunbond material. In an embodiment, a fluid transfer layer 68 can include a meltblown material. In an embodiment, the fluid transfer layer 68 can be a laminate of a meltblown nonwoven material having fine fibers laminated to at least one spunbond nonwoven material layer having coarse fibers. In such an embodiment, the fluid transfer layer 68 can be a spunbond-meltblown ("SM") material. In an embodiment, the fluid transfer layer 68 can be a spunbond-meltblown-spunbond ("SMS") material. A non-limiting example of such a fluid transfer layer 68 can be a 10 gsm SMS material. In various embodiments, the fluid transfer layer 68 can be composed of at least one material which has been hydraulically entangled into a nonwoven substrate. In various embodiments, the fluid transfer layer 68 can be composed of at least two materials which have been hydraulically entangled into a nonwoven substrate. In various embodiments, the fluid transfer layer 68 can have at least three materials which have been hydraulically entangled into a nonwoven substrate. A non-limiting example of a fluid transfer layer 68 can be a 33 gsm hydraulically entangled substrate. In such an example, the fluid transfer layer 68 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 68 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the fluid transfer layer 68. A non-limiting example of a wet strength agent can be Kymene 6500 (557LK) or equivalent available from Ashland Inc. of Ashland, Ky., U.S.A. In various embodiments, a surfactant can be included in the fluid transfer layer 68. In various embodiments, the fluid transfer layer 68 can be hydrophilic. In various embodiments, the fluid transfer layer 68 can be hydrophobic and can be treated in any manner known in the art to be made hydrophilic.

In an embodiment, the fluid transfer layer 68 can be in contact with and/or bonded with an absorbent body 34 which is made at least partially of particulate material such as superabsorbent material. In an embodiment in which the fluid transfer layer 68 at least partially or completely encompasses the absorbent body 34, the fluid transfer layer 68 should not unduly expand or stretch as this might cause the particulate material to escape from the absorbent body 34. In an embodiment, the fluid transfer layer 68, while in a dry state, should have respective extension values at peak load in the machine and cross directions of 30 percent or less and 40 percent or less, respectively.

In an embodiment, the fluid transfer layer 68 may have a longitudinal length the same as, greater than, or less than the longitudinal length of the absorbent body 34. The fluid transfer layer 68 can have a longitudinal length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm.

Acquisition Layer:

In various embodiments the absorbent article 10 can have an acquisition layer 70. The acquisition layer 70 can help decelerate and diffuse surges or gushes of liquid body exudates penetrating the body facing liner 28. In an embodiment, the acquisition layer 70 can be positioned between the body facing liner 28 and the absorbent body 34 to take in and distribute body exudates for absorption by the absorbent body 34. In an embodiment, the acquisition layer 70 can be positioned between the body facing liner 28 and a fluid transfer layer 68 if a fluid transfer layer 68 is present.

In an embodiment, the acquisition layer 70 can be in contact with and/or bonded with the body facing liner 28. In an embodiment in which the acquisition layer 70 is bonded with the body facing liner 28, bonding of the acquisition layer 70 to the body facing liner 28 can occur through the use of an adhesive and/or point fusion bonding, but is not limited to such methods of bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 70 may have any longitudinal length dimension as deemed suitable. The acquisition layer 70 may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer 70 can have any length such that the acquisition layer 70 can be coterminous with the waist edges, 22 and 24, of the absorbent article 10.

In an embodiment, the longitudinal length of the acquisition layer 70 can be the same as the longitudinal length of the absorbent body 34. In such an embodiment the midpoint of the longitudinal length of the acquisition layer 70 can substantially align with the midpoint of the longitudinal length of the absorbent body 34.

In an embodiment, the longitudinal length of the acquisition layer 70 can be shorter than the longitudinal length of the absorbent body 34. In such an embodiment, the acquisition layer 70 may be positioned at any desired location along the longitudinal length of the absorbent body 34. As an example of such an embodiment, the absorbent article 10 may contain a target area where repeated liquid surges typically occur in the absorbent article 10. The particular location of a target area can vary depending on the age and gender of the wearer of the absorbent article 10. For example, males tend to urinate further toward the front waist region 12 of the absorbent article 10 and the target area may be phased forward within the absorbent article 10. For example, the target area for a male wearer may be positioned about 2¾" forward of the longitudinal midpoint of the absorbent body 34 and may have a length of about ±3" and a width of about ±2". The female target area can be located closer to the center of the crotch region 16 of the absorbent article 10. For example, the target area for a female wearer may be positioned about 1" forward of the longitudinal midpoint of the absorbent body 34 and may have a length of about ±3" and a width of about ±2". As a result, the relative longitudinal placement of the acquisition layer 70 within the absorbent article 10 can be selected to best correspond with the target area of either or both categories of wearers.

In an embodiment, the absorbent article 10 may contain a target area centered within the crotch region 16 of the absorbent article 10 with the premise that the absorbent article 10 would be worn by a female wearer. The acquisition layer 70, therefore, may be positioned along the longitudinal length of the absorbent article 10 such that the acquisition layer 70 can be substantially aligned with the target area of the absorbent article 10 intended for a female wearer. Alternatively, the absorbent article 10 may contain a target area positioned between the crotch region 16 and the front waist region 12 of the absorbent article 10 with the premise that the absorbent article 10 would be worn by a male wearer. The acquisition layer 70, therefore, may be positioned along the longitudinal length of the absorbent article 10 such that the acquisition layer 70 can be substantially aligned with the target area of the absorbent article 10 intended for a male wearer.

In an embodiment, the acquisition layer 70 can have a size dimension that is the same size dimension as the target area of the absorbent article 10 or a size dimension greater than the size dimension of the target area of the absorbent article 10. In an embodiment, the acquisition layer 70 can be in contact with and/or bonded with the body facing liner 28 at least partially in the target area of the absorbent article 10.

In various embodiments, the acquisition layer 70 can have a longitudinal length shorter than, the same as, or longer than the longitudinal length of the absorbent body 34. In an embodiment in which the absorbent article 10 is a diaper, the acquisition layer 70 may have a longitudinal length from about 120, 130, 140, 150, 160, 170, or 180 mm to about 200, 210, 220, 225, 240, 260, 280, 300, 310 or 320 mm. In such an embodiment, the acquisition layer 70 may be shorter in longitudinal length than the longitudinal length of the absorbent body 34 and may be phased from the front end edge 40 of the absorbent body 34 a distance of from about 15, 20, or 25 mm to about 30, 35 or 40 mm. In an embodiment in which the absorbent article 10 may be a training pant or youth pant, the acquisition layer 70 may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an embodiment, the acquisition layer 70 may have a longitudinal length shorter than the longitudinal length of the absorbent body 34 and may be phased a distance of from about 25, 30, 35 or 40 mm to about 45, 50, 55, 60, 65, 70, 75, 80 or 85 mm from the front end edge 40 of the absorbent body 34. In an embodiment in which the absorbent article 10 is an adult incontinence garment, the acquisition layer 70 may have a longitudinal length from about 200, 210, 220, 230, 240, or 250 mm to about 260, 270, 280, 290, 300, 320, 340, 360, 380, 400, 410, 415, 425, or 450 mm. In such an embodiment, the acquisition layer 70 may have a longitudinal length shorter than the longitudinal length of the absorbent body 34 and the acquisition layer 70 may be phased a distance of from about 20, 25, 30 or 35 mm to about 40, 45, 50, 55, 60, 65, 70 or 75 mm from the front end edge 40 of the absorbent body 34.

The acquisition layer 70 may have any width as desired. The acquisition layer 70 may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer 70 may vary dependent upon the size and shape of the absorbent article 10 within which the acquisition layer 70 will be placed. The acquisition layer 70 can have a width smaller than, the same as, or larger than the width of the absorbent body 34. Within the crotch region 16 of the absorbent article 10, the acquisition layer 70 can have a width smaller than, the same as, or larger than the width of the absorbent body 34.

In an embodiment, the acquisition layer 70 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 70 can be formed from a material that is substantially hydrophobic, such as a nonwoven web composed of polypropylene, polyethylene, polyester, and the like, and combinations thereof.

Body Facing Liner:

In various embodiments, the body facing liner 28 of the absorbent article 10 can overlay the absorbent body 34 and the backsheet 26 and can isolate the wearer's skin from liquid waste retained by the absorbent body 34. In various embodiments, a fluid transfer layer 68 can be positioned between the body facing liner 28 and the absorbent body 34. In various embodiments, an acquisition layer 70 can be positioned between the body facing liner 28 and the absorbent body 34 or a fluid transfer layer 68, if present. In various embodiments, the body facing liner 28 can be bonded to the acquisition layer 70, or the fluid transfer layer 68 if no acquisition layer 70 is present, via adhesive and/or by a point fusion bonding. The point fusion bonding may be selected from ultrasonic, thermal, pressure bonding, and combinations thereof.

In an embodiment, the body facing liner 28 can extend beyond the absorbent body 34 and/or a fluid transfer layer 68, and/or an acquisition layer 70 to overlay a portion of the backsheet 26 and can be bonded thereto by any method deemed suitable, such as, for example, by being bonded thereto by adhesive, to substantially enclose the absorbent body 34 between the backsheet 26 and the body facing liner 28. The body facing liner 28 may be narrower than the backsheet 26, but it is to be understood that the body facing liner 28 and the backsheet 26 may be of the same dimensions. It is also contemplated that the body facing liner 28 may not extend beyond the absorbent body 34 and/or may not be secured to the backsheet 26. It is further contemplated that the body facing liner 28 may be composed of more than one segment of material. The body facing liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The body facing liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the body facing liner 28. The body facing liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof.

For example, the body facing liner 28 can be composed of a meltblown or spunbond web of polyolefin fibers. Alternatively, the body facing liner 28 can be a bonded-carded web composed of natural and/or synthetic fibers. The body facing liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire body facing liner 28 or it can be selectively applied to particular sections of the body facing liner 28.

In an embodiment, a body facing liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a body facing liner 28 can be a spunbond substrate with a basis weight from about 10 or 12 to about 15 or 20 gsm. In an embodiment, a body facing liner 28 can be a 12 gsm spunbond-meltblown-spunbond substrate having 10% meltblown content applied between the two spunbond layers.

Although the backsheet 26 and body facing liner 28 can include elastomeric materials, it is contemplated that the backsheet 26 and the body facing liner 28 can be composed of materials which are generally non-elastomeric. In an embodiment, the body facing liner 28 can be stretchable, and more suitably elastic. In an embodiment, the body facing liner 28 can be suitably stretchable and more suitably elastic in at least the lateral or circumferential direction of the absorbent article 10. In other aspects, the body facing liner 28 can be stretchable, and more suitably elastic, in both the lateral and the longitudinal directions 32, 30, respectively.

Containment Flaps:

In an embodiment, containment flaps, 44, 46, can be secured to the body facing liner 28 of the absorbent article 10 in a generally parallel, spaced relation with each other to provide a barrier against the flow of body exudates to the leg openings. In an embodiment, the containment flaps, 44, 46, can extend longitudinally from the front waist region 12 of the absorbent article 10, through the crotch region 16 to the back waist region 14 of the absorbent article 10.

Figure 4:
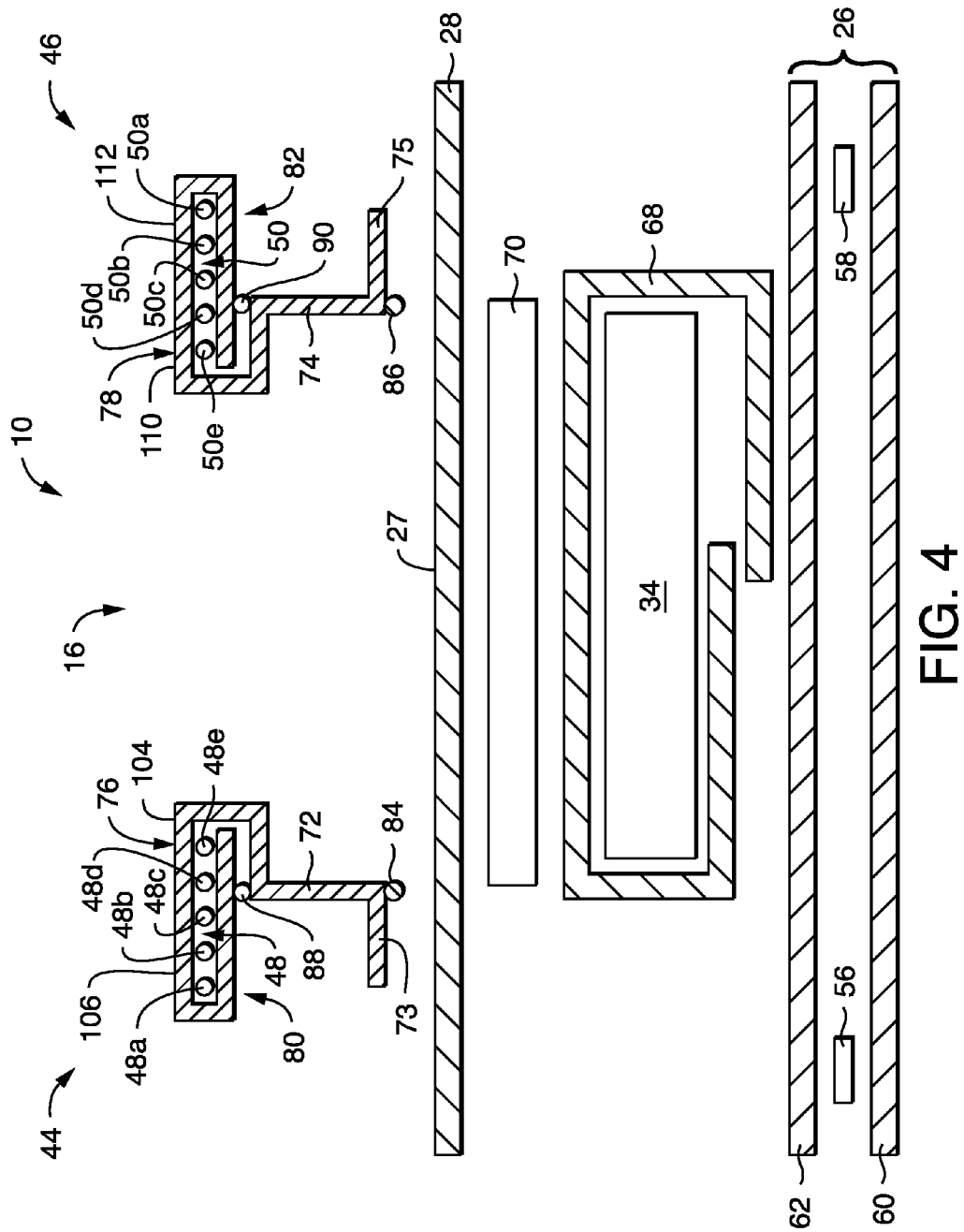
FIG. 4 is a cross-section, exploded view of a crotch region of the absorbent article of FIG. 1 taken when the absorbent article is in a relaxed condition.
Figure 5:
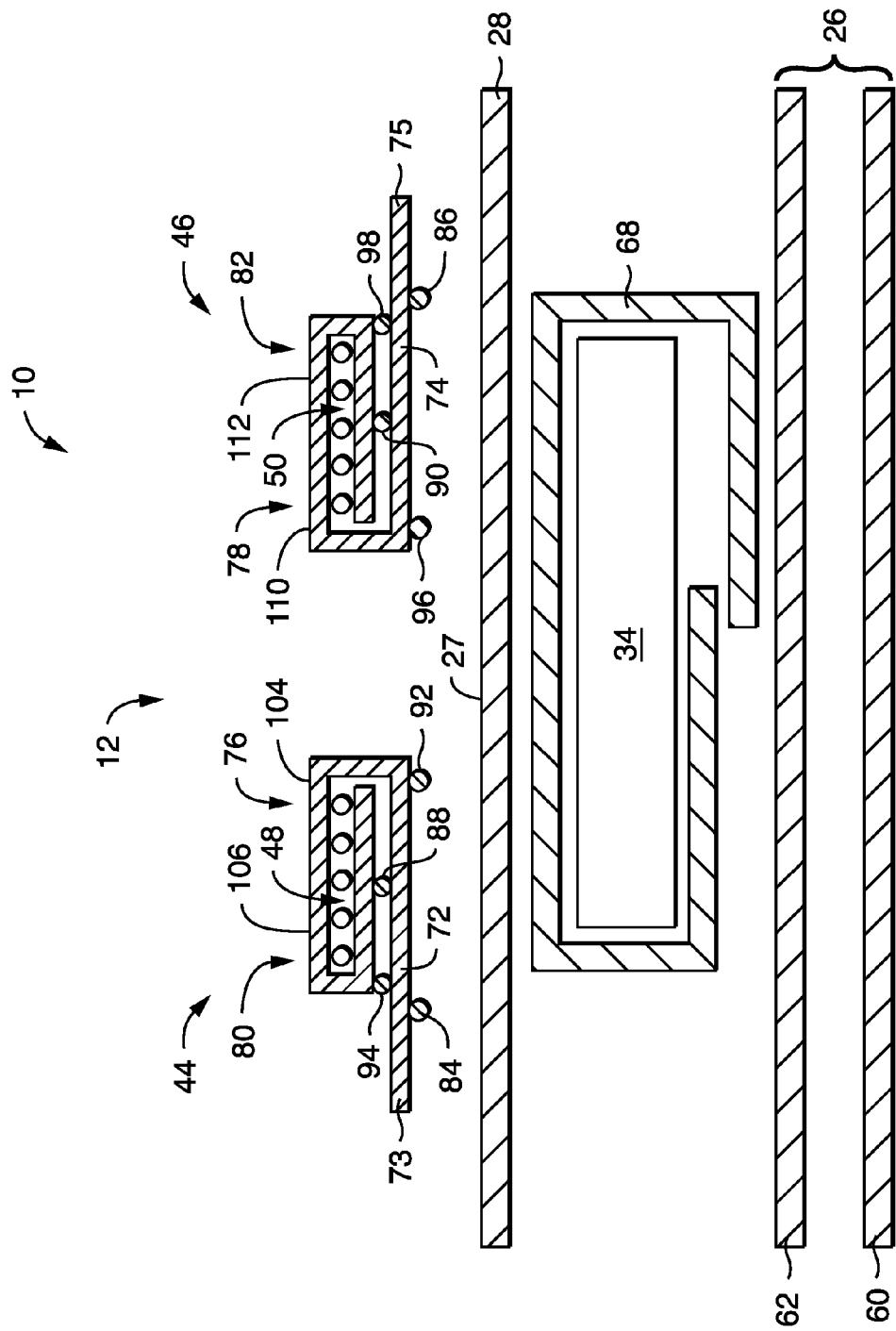
FIG. 5 is a cross-section, exploded view of a front waist region of the absorbent article of FIG. 1 taken when the absorbent article is in a relaxed condition.
Figure 6:
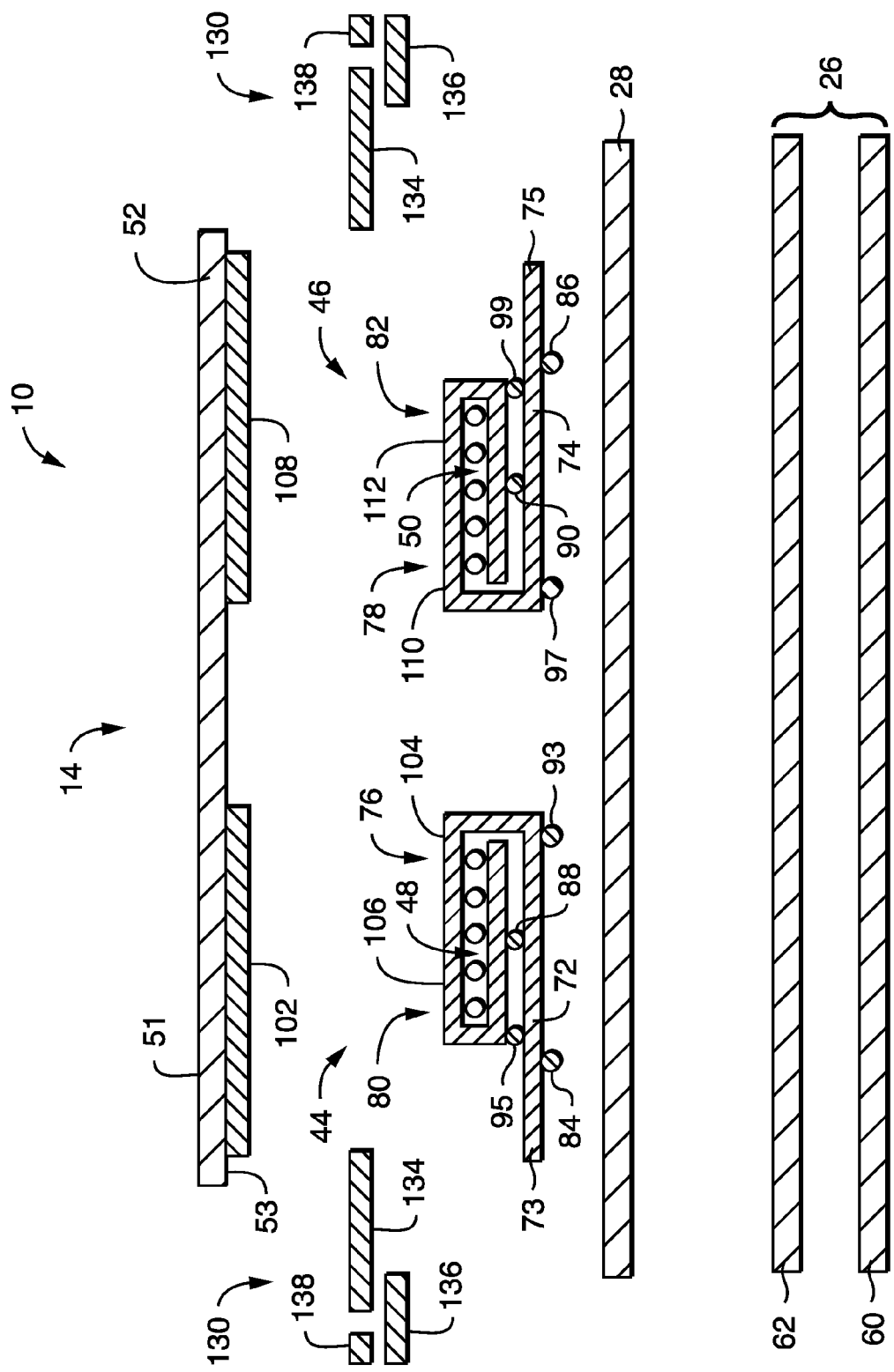
FIG. 6 is a cross-section, exploded view of a rear waist region of the absorbent article of FIG. 1 taken when the absorbent article is in a relaxed condition.

With reference to FIGS. 4-6, the containment flaps, 44, 46 can each include a stem 72, 74, an inner flap projection 76, 78, and an outer flap projection 80, 82. Each containment flap 44, 46 can also include a foot portion 73, 75. As illustrated in FIG. 4, which shows an exploded, cross-sectional view of the absorbent article 10 when the absorbent article 10 is in a relaxed condition, the stem 72, 74 of each containment flap 44, 46 can be bonded to the body facing liner 28 with adhesive 84, 86 that bonds the entire length of the containment flap 44, 46 to the body facing liner 28. However, other bonding methods and applications are contemplated for bonding each containment flap 44, 46 to the body facing liner 28, including, but not limited to, pressure bonding and ultrasonic bonding. Additionally, each containment flap 44, 46 can be bonded to other components of the absorbent article 10 other than the body facing liner 28, including, but not limited to, the back sheet 26.

The stem 72, 74 of each containment flap 44, 46 is configured to extend away from the body facing surface 27 of the body facing liner 28 and the backsheet 26 when the absorbent article is in a relaxed condition and fitted on the wearer, especially in the crotch region 16, as will be explained further below. As such, the stem 72, 74 provides lateral containment of body exudates. Although the stem 72, 74 of each containment flap 44, 46 is depicted as extending substantially perpendicularly away from the body facing surface 27 of the body facing liner 28, the stem 72, 74 can extend away from the body facing surface 27 at different angles and still be within the scope of this disclosure. The stems 72, 74 of the containment flaps 44, 46 can be positioned laterally inward from the longitudinal side edges 18, 20, respectively. The transition between the stem 72, 74 and the foot portion 73, 75 of each containment flap 44, 46, respectively, can be defined by the point of bonding of the stem 72, 74 to a component of the absorbent article that allows the stem 72, 74 to extend away from that attached component of the absorbent article 10. For example, in the embodiment depicted in FIG. 4, the adhesive 84, 86 that bonds the containment flap 44, 46 to the body facing liner 28 can define the transition between stem 72, 74 and the foot portion 73, 75 of each containment flap 44, 46. When the absorbent article 10 is in the relaxed condition, the stem 72, 74 extends from such point of bonding away from the body facing surface 27 of the body facing liner 28 to the intersection with inner flap projection 76, 78 and the outer flap projection 80, 82. In one embodiment, the stem 72, 74 can be about 5 mm to about 50 mm in height as measured in the crotch region 16 in a cross-sectional configuration when the absorbent article 10 is in the relaxed condition, preferably between about 10 mm and about 40 mm in height, and more preferably about 25 mm in height.

The foot portion 73, 75 of each containment flap 44, 46 can extend to the longitudinal side edges 18, 20 of the absorbent article 10, however, the foot portion 73, 75 need not extend to the longitudinal side edges 18, 20 of the absorbent article 10, as depicted in FIG. 2. In an embodiment where the foot portion 73, 75 does extend to the longitudinal side edges 18, 20, the foot portion 73, 75 can be bonded at more than one point to the body-facing liner 28 or the backsheet 26. For example, adhesive could be used to bond the foot portion 73, 75 to the body facing liner 28 or the backsheet 26 near the stem 72, 74 and further adhesive could be used to bond the foot portion 73, 75 to the body facing liner 28 or the backsheet 26 near the longitudinal side edges 18, 20. Alternatively, the entire foot portion 73, 75 could be bonded to the body facing liner 28 and/or the backsheet 26. Additionally, in an embodiment where the foot portion 73, 75 extends to the longitudinal side edges 18, 20, a portion of the foot portion 73, 75 can be cut-out as part of forming the leg-cutout of the absorbent article 10. Thus, the length of the foot portion 73, 75 can vary between different embodiments. In an embodiment where the foot portion 73, 75 does not extend to the longitudinal side edges 18, 20, the foot portion 73, 75 can be about 2 mm to about 20 mm in length as measured in the lateral direction 32 in the crotch region 16, more preferably about 5 mm to about 15 mm in length.

The inner flap projection 76, 78 of each containment flap 44, 46 extends laterally from the stem 72, 74 towards the longitudinal axis 29 of the absorbent article 10 when the absorbent article 10 is in a relaxed condition, as illustrated in FIG. 4. The outer flap projection 80, 82 of each containment flap 44, 46 extends laterally from the stem 72, 74 away from the longitudinal axis 29 of the absorbent article 10 when the absorbent article 10 is in a relaxed condition, as illustrated in FIG. 4. For purposes herein, the inner flap projections 76, 78 can be distinguished from the outer flap projections 80, 82 of each containment flap 44, 46 at the junction of the inner flap projection 76 and the outer flap projection 80 at the stem 72 and the junction of the inner flap projection 78 and the outer flap projection 82 at the stem 74. Adhesive 88 can be used to bond the stem 72 to the inner flap projection 76 and the outer flap projection 80 of the containment flap 44 and adhesive 90 can be used to bond the stem 74 to the inner flap projection 78 and the outer flap projection 82 of the containment flap 46. Of course, the inner flap projections, 76, 78 and the outer flap projections 80, 82 can be bonded to the stems 72, 74, respectively, by other bonding methods known in the art, including, but not limited to, pressure bonding and ultrasonic bonding. The inner flap projections 76, 78 and the outer flap projections 80, 82 can be of equal or different lengths than one another. The length of the inner flap projection 76 and the outer flap projection 80 of the containment flap 44 as measured in the lateral direction 32 can be about 5 mm to about 50 mm, preferably about 10 mm to about 40 mm, and more preferably about 20 mm to about 30 mm. Similarly, the length of the inner flap projection 78 and the outer flap projection 82 of the containment flap 46 as measured in the lateral direction 32 can be about 5 mm to about 50 mm, preferably about 10 mm to about 40 mm, and more preferably about 20 mm to about 30 mm.

At least a portion of the inner flap projection 76, 78 and the outer flap projection 80, 82 of each containment flap 44, 46 can be elasticized. The inner flap projections 76, 78 and the outer flap projections 80, 82 can be elasticized in various ways. For example, in the embodiment depicted in FIG. 4, each containment flap 44, 46 includes an elastic member 48, 50. The elastic member 48, 50 can be any elastomeric material capable of being elongated at least about 50 percent, desirably about 350 percent, and capable of recovering to within at least about 250 percent, and desirably about 150 percent of its original length after being elongated about 300 percent. The elastic member 48, 50 could be a spandex elastomeric strand(s) such as, for example, a LYCRA thread commercially available from E. I. DuPont de Nemours and Co. Alternatively, the elastic member 48, 50 can be composed of a thermoplastic elastomer or a natural or a synthetic rubber commercially available from J.P.S. Elastomerics Corp. Alternatively, the elastic member 48, 50 can also be composed of a heat activated elastic material such as PEBAX, commercially available from Atochem, Inc., which can be activated with heat treatment after the elastic member 48, 50 is secured to the containment flap 44, 46. As will be discussed further below, the elastic member 48, 50 can be attached to the containment flap 44, 46 by any method known to those skilled in the art, such as thermal bonding, adhesive bonding, ultrasonic bonding or the like.

In the embodiments depicted herein, each containment flap 44, 46 includes an elastic member 48, 50. The elastic member 48 in the containment flap 44 can be a series of five elastic strands 48a, 48b, 48c, 48d, 48e and the elastic member 50 in the containment flap 46 can be a series of five elastic strands 50a, 50b, 50c, 50d, 50e, as depicted in FIGS. 2-6. The inner flap projection 76 of the containment flap 44 includes elastic strands 48d and 48e and the inner flap projection 78 of the containment flap 46 includes elastic strands 50d and 50e. The outer flap projection 80 of the containment flap 44 includes elastic strands 48a and 48b.

The outer flap projection 82 of the containment flap 46 includes elastic strands 50a and 50b. In the embodiment illustrated in FIG. 4, the elastic strand 48c and the elastic strand 50c of elastic members 48, 50, respectively, is generally positioned above the stem 72, 74, and thus, is at the junction between the inner flap projection 76 and outer flap projection 80 of the containment flap 44 and at the junction between the inner flap projection 78 and the outer flap projection 82. As such, the elastic strand 48c can be considered to be partially within both the inner flap projection 76 and the outer flap projection 80 of containment flap 44 and the elastic strand 50c can be considered to be partially within both the inner flap projection 78 and the outer flap projection 82 of containment flap 46.

Of course, modifications to the way in which the inner flap projections 76, 78 and the outer flap projections 80, 82 can be elasticized can be made by one of ordinary skill in the art and are within the scope of this disclosure. For example, it is contemplated that the elastic member 48 of the first containment flap 44 and/or the elastic member 50 of the second containment flap 46 could include fewer than five elastic strands or more than five elastic strands. Alternatively and/or additionally, the inner flap projections 76, 78 could include other types of elastic materials, such as elastic ribbons. Alternatively and/or additionally, the inner flap projections 76, 78 and the outer flap projections 80, 82 can be elasticized by being composed of a material exhibiting substantially elastic properties.

Referring to FIG. 5, a cross-sectional exploded view of a front waist region 12 of the absorbent article 10 is shown. The inner flap projections 76, 78 and the outer flap projections 80, 82 of the containment flaps 44, 46 can each be secured in at least a portion of the front waist region 12. In the embodiment illustrated in FIG. 5, the inner flap projection 76 of the containment flap 44 can be secured by being bonded to the body facing liner 28 with adhesive 92. The outer flap projection 80 of the containment flap 44 can be secured by being bonded to the stem 72 with adhesive 94. Similarly, the inner flap projection 78 of the containment flap 46 can be secured by being bonded to the body facing liner 28 with adhesive 96 and the outer flap projection 82 of the containment flap 46 can be secured by being bonded to the stem 74 with adhesive 98.

By securing the inner flap projections 76, 78 of the containment flaps 44, 46 in the front waist region 12, the tendency is reduced for the inner flap projections 76, 78 to curl back towards the stem 72, 74 due to the tension in the elastic members 48, 50 when the absorbent article 10 is in a stretched condition, such as when the absorbent article 10 is being applied to and/or worn by the wearer. Similarly, by securing the outer flap projections 80, 82 of the containment flaps 44, 46 in the front waist region 12, the tendency is reduced for the outer flap projections 80, 82 to curl towards the longitudinal axis 29 and towards the stem 72, 74 due to the elastic members 48, 50 when the absorbent article 10 is in a stretched condition. This can help to maintain the upper surfaces 104, 110 of the inner flap projections 76, 78 and the upper surfaces 106, 112 of the outer flap projections 80, 82 remain level which can provide increased contact area of the upper surfaces 104, 106 of the containment flap 44 and the upper surfaces 110, 112 of the containment flap 46 with the wearer's skin. This securing can also help prevent the inner flap projection 76 and the outer flap projection 80 of the containment flap 44 and the inner flap projection 78 and the outer flap projection 82 of the containment flap 44 from folding over on one another as the absorbent article 10 is stretched and applied to the wearer. As a result, the containment flaps 44, 46 can provide more contact with the wearer's skin to provide improved gasketing benefits of body exudates and less irritation on the wearer's skin by increasing the area of contact between the containment flaps 44, 46 and the wearer's skin as compared to certain containment flaps of the prior art.

Referring to FIG. 6, a cross-sectional exploded view of a rear waist region of the absorbent article is shown. Similar to the discussion above related to FIG. 5 and the front waist region, the inner flap projections 76, 78 and the outer flap projections 80, 82 of the containment flaps 44, 46 can also each be secured in at least a portion of the rear waist region 14. The inner flap projection 76 of the containment flap 44 can be secured by being bonded to the body facing liner 28 with adhesive 93. The outer flap projection 80 of the containment flap 44 can be secured by being bonded to the stem 72 with adhesive 95. Similarly, the inner flap projection 78 of the containment flap 46 can be secured by being bonded to the body facing liner 28 with adhesive 97 and the outer flap projection 82 of the containment flap 46 can be secured by being bonded to the stem 74 with adhesive 99.

The rear waist elastic member 52 can provide an additional or alternative means for securing the inner flap projections 76, 78 and the outer flap projections 80, 82 of the containment flaps 44, 46 in the rear waist region 12 for reducing the outer flap projections 80, 82 from curling towards the longitudinal axis 29 in the crotch region 16 and for reducing the inner flap projections 76, 78 from curling away from the longitudinal axis 29 in the crotch region 16. The rear waist elastic member 52 has a body facing surface 51 and a garment facing surface 53. The overlap of the garment facing surface 53 of the rear waist elastic member 52 with the inner flap projections 76, 78 and the outer flap projections 80, 82 of the containment flaps 44, 46 can secure the inner flap projections 76, 78 and the outer flap projections 80, 82 in the rear waist region 12. Additionally, adhesive 102 applied to the garment facing surface 53 of the rear waist elastic member 52 can further secure the inner flap projection 76 and the outer flap projection 80 of the containment flap 44 by bonding to an upper surface 104 of the inner flap projection 76 and an upper surface 106 of the outer flap projection 80. Similarly, adhesive 108 applied to the garment facing surface 53 of the rear waist elastic member 52 can further secure the inner flap projection 78 and the outer flap projection 82 of the containment flap 46 by bonding to an upper surface 110 of the inner flap projection 78 and an upper surface 112 of the outer flap projection 82.

As noted above with respect to the front waist region 12, securing the inner flap projections 76, 78 of the containment flaps 44, 46 in the rear waist region 14 reduces the tendency for the inner flap projections 76, 78 to curl back towards the stem 72, 74 and away from the longitudinal axis 29 due to tension in the elastic members 48, 50 when the absorbent article 10 is in a stretched condition, such as when the absorbent article 10 is being applied to and/or worn by the wearer. Similarly, securing the outer flap projections 80, 82 of the containment flaps 44, 46 in the front waist region 12 reduces the tendency for the outer flap projections 80, 82 to curl towards the longitudinal axis 29 and towards the stem 72, 74 due to the elastic members 48, 50 when the absorbent article 10 is in a stretched condition. This can help level the upper surfaces 104, 110 of the inner flap projections 76, 78 and the upper surfaces 106, 112 of the outer flap projections 80, 82 and increase the area of contact of the containment flaps 44, 46 against the wearer's skin. This securing can also help prevent the inner flap projection 76 and the outer flap projection 80 of the containment flap 44 and the inner flap projection 78 and the outer flap projection 82 of the containment flap 44 from folding over on one another as the absorbent article 10 is stretched and applied to the wearer. As a result, the containment flaps 44, 46 can provide more contact with the wearer's skin to provide improved gasketing benefits of body exudates and less irritation on the wearer's skin by increasing the area of contact between the containment flaps 44, 46 and the wearer's skin as compared to certain containment flaps of the prior art.

It is also contemplated that the inner flap projections 76, 78 and the outer flap projections 80, 82 can be secured in the front waist region 12 and the rear waist region 14 with different bonding methods and different bonding orientations and still be within the scope of this disclosure. For example, the inner flap projections 76, 78 and the outer flap projections 80, 82 can be secured in the front waist region 12 and/or the rear waist region 14 by pressure bonding or ultrasonic bonding the outer flap projections 80, 82 to the stem 72, 74 and the inner flap projections 76, 78 to the body facing liner 28. Additionally, depending on the orientation of the containment flaps 44, 46, the inner containment flaps 76, 78 could be bonded to the stem 72, 74, respectively, in the front waist region 12 and/or the rear waist region 14 and the outer containment flaps 80, 82 could each be bonded to the body facing liner 28 in the front waist region 12 and/or the rear waist region 14.

During manufacture of the containment flaps 44, 46, at least a portion of the elastic members 48, 50 can be bonded to the containment flaps 44, 46 while the elastic members 48, 40 are elongated. The percent elongation of the elastic members 48, 50 can be, for example, about 110% to about 350%. In one embodiment, the elastic members 48, 50 can be coated with adhesive while elongated for a specified length prior to attaching to the elastic members 48, 50 to the containment flaps 44, 46. In a stretched condition, the length of the elastic members 48, 50 which have adhesive coupled thereto can provide an active flap elastic region 114 in the containment flap 44 and an active flap elastic region 116 in the containment flap 46, as best shown in FIG. 2, which will gather upon relaxation of the absorbent article 10, as discussed below. The active flap elastic region 114 of containment flap 44 can include a front end 118 and a rear end 120. The front end 118 and the rear end 120 of the active flap elastic region 114 can be inside of the front waist edge 22 and the rear waist edge 24, respectively, to provide an active flap elastic region 114 that is shorter than a length of the absorbent article 10, as depicted in FIG. 2. The active flap elastic region 116 of containment flap 46 can include a front end 122 and a rear end 124. The front end 122 and the rear end 124 of the active flap elastic region 116 can be inside of the front waist edge 22 and the rear waist edge 24, respectively, to provide an active flap elastic region 116 that is shorter than a length of the absorbent article 10, as depicted in FIG. 2. In this exemplary method of bonding the elastic members 48, 50 to the containment flaps 44, 46, the portion of the elastic members 44, 46 not coated with adhesive, specifically in the front end region 12 and rear end region 14 of the absorbent article 10, will retract after the elastic members 48, 50 and the absorbent article 10 are cut in manufacturing to form an individual absorbent article 10. The relaxing of the elastic members 48, 50 in the active flap elastic region 114, 116 when the absorbent article 10 is in a relaxed condition can cause each containment flap 44, 46 to gather and cause the stem 72, 74 of each containment flap 44, 46 to extend away from the body facing liner 28 and backsheet 26 in the crotch region 16, as depicted in FIG. 4.

The elastic members 48, 50 can be bonded to the containment flaps 44, 46 in various other ways as known by those of skill in the art to provide an active flap elastic region 114, 116, which is within the scope of this disclosure. Additionally, the active flap elastic regions 114, 116 can be shorter than depicted in FIG. 2 or can be longer than depicted in FIG. 2, including extending to the front waist edge 22 and the rear waist edge 24, and still be within the scope of this disclosure.

FIG. 2 illustrates the adhesives 92, 96 that are used to bond the inner flap projections 76, 78 to the body facing liner 28 in the front waist region 12, respectively, and the adhesives 93, 97 that are used to bond the inner flap projections 76, 78 to the body facing liner 28 in the rear waist region 14, respectively. Additionally, FIG. 2 illustrates the adhesives 94, 98 that are used to bond the outer flap projections 80, 82 to the stem 72, 74 in the front waist region 12, respectively, and the adhesives 95, 99 that are used to bond the outer flap projections 80, 82 to the stem 72, 74 in the rear waist region 14, respectively. The representation of adhesives 92, 93, 94, 95, 96, 97, 98 with dashed lines in FIG. 2 is meant to portray these adhesives are hidden in the top view depicted in FIG. 2 and is not meant to limit these adhesives to being applied only intermittently where they are currently illustrated in the front waist region 12 and the rear waist region 14, although such an intermittent application is contemplated and within the scope of this disclosure. Furthermore, the dashed line representation for the adhesives 84, 86 that bond the stems 72, 74 to the body facing liner 28, respectively, is also meant to portray that these adhesives are hidden in the top view depicted in FIG. 2, and are not meant to limit these adhesives to being applied intermittently along the length of the absorbent article 10, although such an intermittent application is contemplated and within the scope of this disclosure.

As shown in FIG. 2, the portion of the inner flap projections 76, 78 that are bonded to the body facing liner 28 in the front waist region 12 can be equal to the portion of the outer flap projections 80, 82 that are bonded to the stem 72, 74 in the front waist region 12. Additionally, the portion of the inner flap projections 76, 78 that are bonded to the body facing liner 28 in the rear waist region 14 can be equal to the portion of the outer flap projections 80, 82 that are bonded to the stem 72, 74 in the rear waist region 14. Furthermore, in the embodiment illustrated in FIG. 2, the portion of the inner flap projection 76 and the portion of the outer flap projection 80 of the containment flap 44 that are bonded to the body facing liner 28 and the stem 72, respectively, in the front waist region 12 can extend from substantially the front waist edge 22 to substantially the front end 116 of the active flap elastic region 114. Additionally, the portion of the inner flap projection 78 and the portion of the outer flap projection 82 of the containment flap 46 that are bonded to the body facing liner 28 and the stem 74, respectively, in the front waist region 12 can extend from substantially the front waist edge 22 to the front end 122 of the active flap elastic region 116. By providing adhesives 92, 94 on the containment flap 44 and adhesives 96, 98 on the containment flap 46 in the front waist region 12 to the front end 116 of the active flap elastic region 114 assists in reducing the tendency of and/or the amount that the inner flap projections 76, 78 and the outer flap projections 80, 82 may curl towards the stems 72, 74 when the absorbent article 10 is in a stretched condition, as noted above. Of course, other configurations of bonding the outer flap projections 80, 82 and/or the inner flap projections 76, 78 of the containment flaps 44, 46 in the front waist region 12 and/or the rear waist region 14 are within the scope of this disclosure.

The containment flaps, 44 and 46, can be constructed of a fibrous material which can be similar to the material forming the body facing liner 28, including, but not limited to a spunbond-meltblown-spunbond ("SMS") material. As discussed above, suitable elastic materials for the flap elastic members, 48 and 50, can include, but are not limited to, spandex elastomeric strands, sheets, strands, or ribbons of natural or synthetic rubber, thermoplastic elastomeric materials, or heat activated elastomeric materials.

Figure 7:
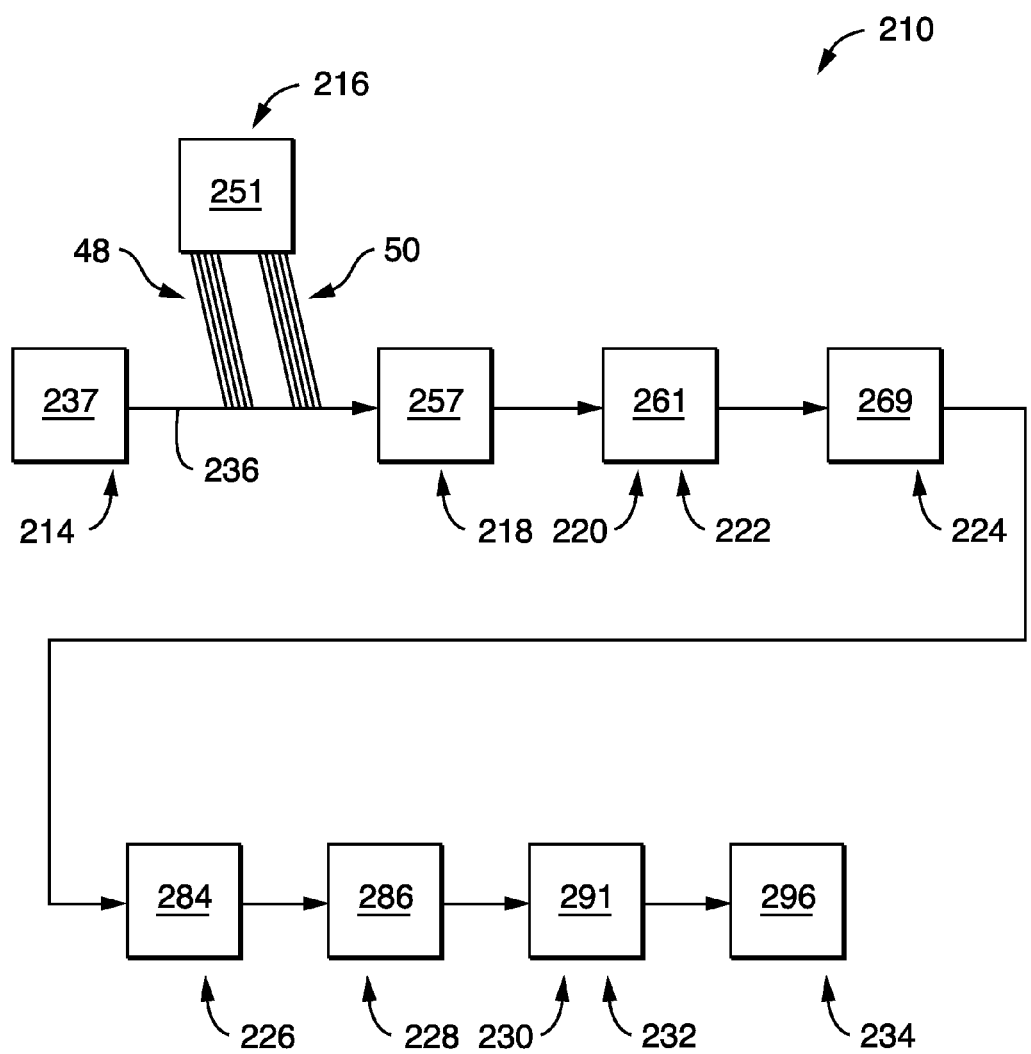
FIG. 7 is a process diagram showing an exemplary method of forming a containment system for an absorbent article shown in FIGS. 1-6.

With reference to FIGS. 7-15, an exemplary method 210 for forming a containment system for an absorbent article 10 including containment flaps 44, 46, as discussed above and as shown in FIGS. 2-6, will now be discussed. FIG. 7 provides a process diagram outlining exemplary steps 214, 216, 218, 220, 222, 224, 226, 228, 230, 232, and 234 that can be part of method 210. While the steps of the method 210 will be discussed in the order of one exemplary embodiment, it is intended that the any steps of the method 210 not be limited to such order, or even required, unless explicitly specified herein.

With reference to FIGS. 7 and 8, the method 210 can include providing a substrate 236 in step 214 from a source 237. The source 237 of the substrate 236 can be from a roll of material, as is known by one of ordinary skill in the art. The substrate 236 can include a first surface 238 and a second surface 240, with the first surface 238 being opposite of the second surface 240. The substrate 236 can also include a first half 242 and a second half 244 that are joined to one another, but divided by a centerline 246. The first half 242 can be on a first side 248 of the centerline 246 and the second half 244 can be on a second side 250 of the centerline 246. For purposes herein, the first half 242 of the substrate 236 can be considered a first substrate and the second half 244 of the substrate 236 can be considered a second substrate despite the first half 242 and the second half 244 being shown as being joined to one another in FIG. 8 in step 214. Alternatively, the first half 242 and the second half 244 can be provided as two substrates physically separate from one another at centerline 246 in step 214. Thus, for purposes of discussion herein, references to the first half 242 of the substrate 236 and to the second half 244 of the substrate 236 could be considered references to a first substrate and a second substrate.

Referring to FIGS. 7 and 9, elastic members 48, 50 from a source of elastics 251 can be applied to the first surface 238 of the substrate 236 in step 216. The elastic member 48 can be applied and attached to the second half 244 of the substrate 236 and the elastic member 50 can be applied and attached to the first half 242 of the substrate 236. The elastic members 48, 50, as discussed above, can be a singular member or multiple members. In one embodiment, the elastic member 48 can include five individual elastic strands 48a, 48b, 48c, 48d, 48e and the elastic member 50 can include five individual elastic strands 50a, 50b, 50c, 50d, 50e. The individual elastic strands 48a, 48b, 48c, 48d, 48e of elastic member 48 can be aligned substantially parallel to one another. The elastic strands 48a, 48b, 48c, 48d, 48e can be spaced about 5 mm from one another in the lateral direction 32. Similarly, the individual elastic strands 50a, 50b, 50c, 50d, 50e can be aligned substantially parallel to one another. The elastic strands 50a, 50b, 50c, 50d, 50e can be spaced about 5 mm from one another in the lateral direction 32. As previously discussed, a specified length of the elastic members 48, 50 can be coated with adhesive prior to their application to the substrate 236 and the elastic members 48, 50 can also be tensioned during their application to the substrate 236, as previously noted above. The length of the adhesive that is coated on the elastic members 48, 50 can define the active flap elastic regions 114, 116 on the containment flaps 44, 46, as discussed above.

Figure 10:
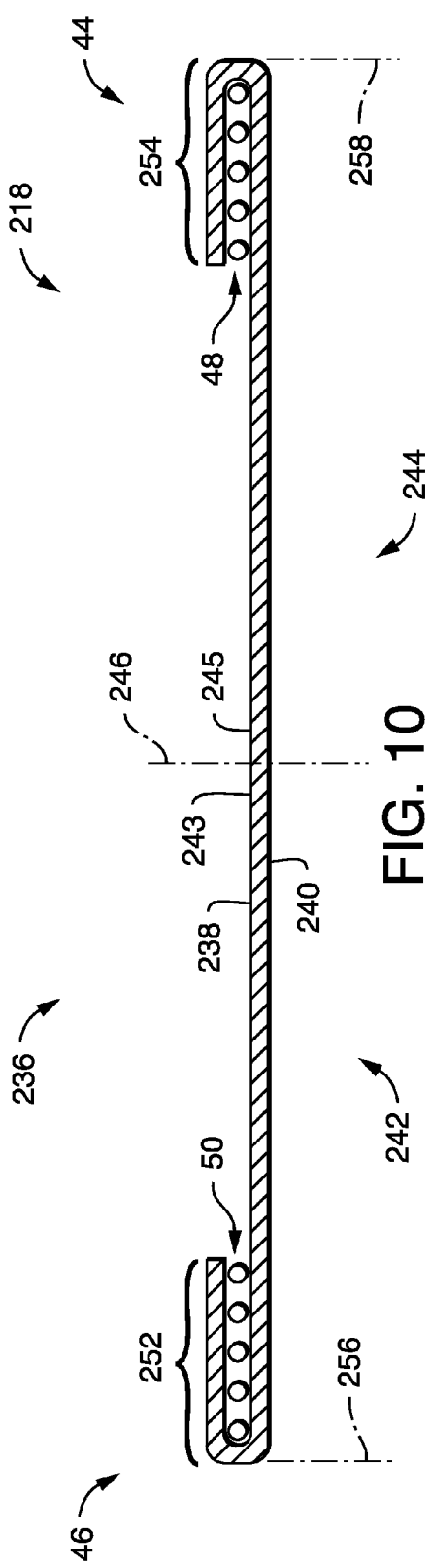
FIG. 10 is a cross-section view of a step of the method shown in FIG. 7.

With reference to FIGS. 7, 9, and 10, the method 210 can include a further step 218. In step 218, a first portion 252 of the first half 242 of the substrate 236 can be folded over the elastic member 50 at fold line 256 by a folding apparatus 257 towards the centerline 246 and towards the proximal end 243 of the first half 242 of the substrate 236. Similarly, a first portion 254 of the second half 244 of the substrate 236 can be folded over the elastic member 48 at fold line 258 by the folding apparatus 257 towards the centerline 246 and towards the proximal end 245 of the second half 244 of the substrate 236. The folding apparatus 257 can be equipment known to one of ordinary skill in the art, such as a folding board. The adhesive coating on the elastic members 50, 48 can bond the first portions 252, 254 to the elastic members 50, 48, respectively, with the elastic members 48 and 50 being in tension, as discussed above. As an alternative to applying adhesive directly to the elastic members 50, 48, adhesive could be applied to the first portions 252, 254 of the substrate 236 to bond the first portions 252, 254 to the elastic members 50, 48, respectively, as the first portions 252, 254 are folded on to the elastic members 50, 48, respectively. Additionally and/or alternatively, the first portions 252, 254 can be bonded to the first half 242 and the second half 244 of the substrate 236, respectively, by other bonding methods after being folded, including, but not limited to, pressure bonding and ultrasonic bonding.

Figure 11:
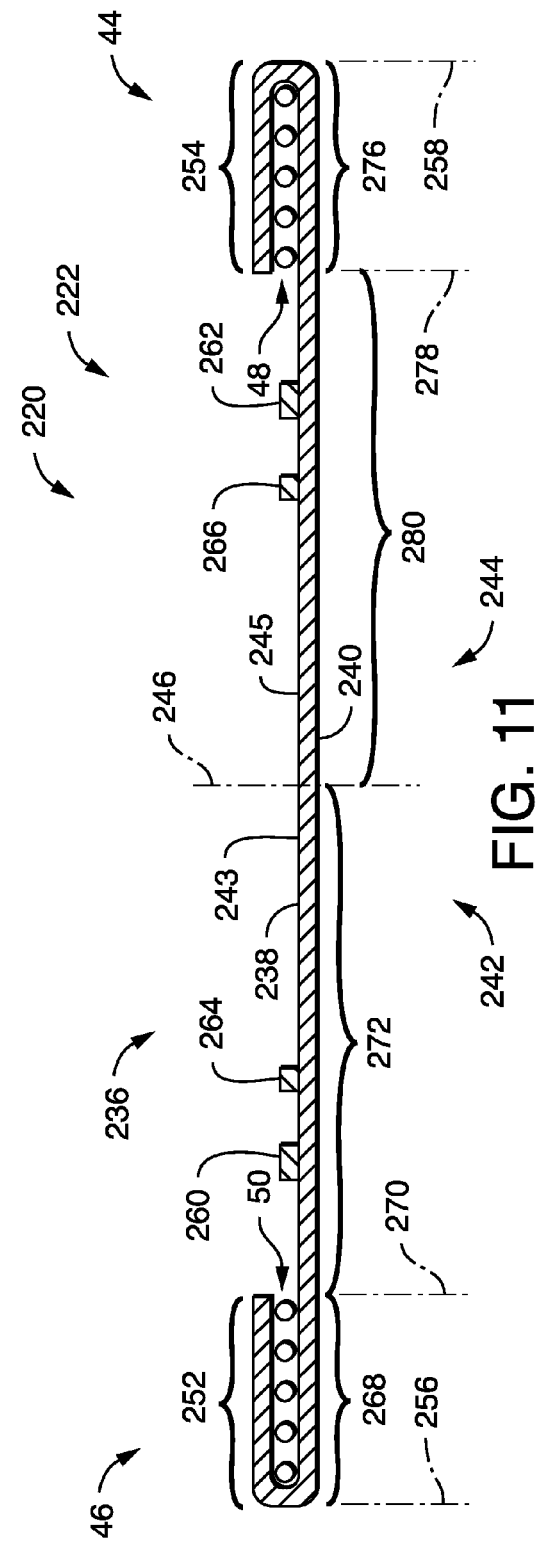
FIG. 11 is a cross-section view of a step of the method shown in FIG. 7.

Referring to FIGS. 7 and 11, the method 210 can also include step 220. Adhesive 260 can be applied to the first half 242 of the substrate 236 in a position to engage the first portion 252 of the first half 242 of the substrate 236. Adhesive 262 can be applied to the second half 244 of the substrate 236 in a position to engage the first portion 254 of the second half 244 of the substrate 236. Adhesives 260, 262 can be applied by an adhesive applicator 261 as is known by one of ordinary skill in the art. As non-limiting examples, the adhesives 260, 262 can be applied with an adhesive head extruding a slot coat or by a spray nozzle providing a spray. As illustrated in FIG. 11, the adhesive 260 can be applied to first surface 238 on the first half 242 of the substrate 236 not directly on the first portion 252 of the first half 242, but in a position to engage the first portion 252 of the first half 242 of the substrate 236 in a further folding step 224, which will be discussed below. Similarly, the adhesive 262 can be applied to the first surface 238 on the second half 244 of the substrate 236 not directly on the first portion 254 of the second half 244, but in a position to engage the first portion 254 of the second half 244 of the substrate in a further folding step 224. Alternatively, the adhesives 260, 262 could be applied directly to the first portions 252, 254, respectively, on the second surface 240 of the substrate 236. Step 220 can be performed after step 218, or after step 216 and prior to step 218, or prior to step 216 and step 218.

Step 222 illustrated in FIGS. 7 and 11 can include applying an intermittent adhesive 264 to the first half 242 of the substrate 236 in a position to engage the first portion 252 of the first half 242 of the substrate 236 near the fold line 256. Furthermore, step 222 can include applying an intermittent adhesive 266 to the second half 244 of the substrate 236 in a position to engage the first portion 254 of the second half 244 of the substrate 236 near the fold line 258. The intermittent adhesives 264, 266 can be applied by the adhesive applicator 261 at the same time as adhesives 260, 262 are being applied to the substrate 236 in step 220, however, the method 210 is not limited to such a configuration. Step 222 could be performed prior to step 220, after step 218 and prior to step 220, after step 216 and prior to step 218, or prior to steps, 216, 218, and 220. As illustrated in FIG. 11, the intermittent adhesive 264 can be applied to the first surface 238 on the first half 242 of the substrate 236 and closer to the centerline 246 than the adhesive 260. Intermittent adhesive 266 can be applied to the first surface 238 on the second half 244 of the substrate and closer to the centerline 246 than the adhesive 262. However, the intermittent adhesives 264, 266 could alternatively be applied directly to the first portions 252, 254, respectively, on the second surface 240 of the substrate 236 near the fold lines 256, 258, respectively.

Figure 12:
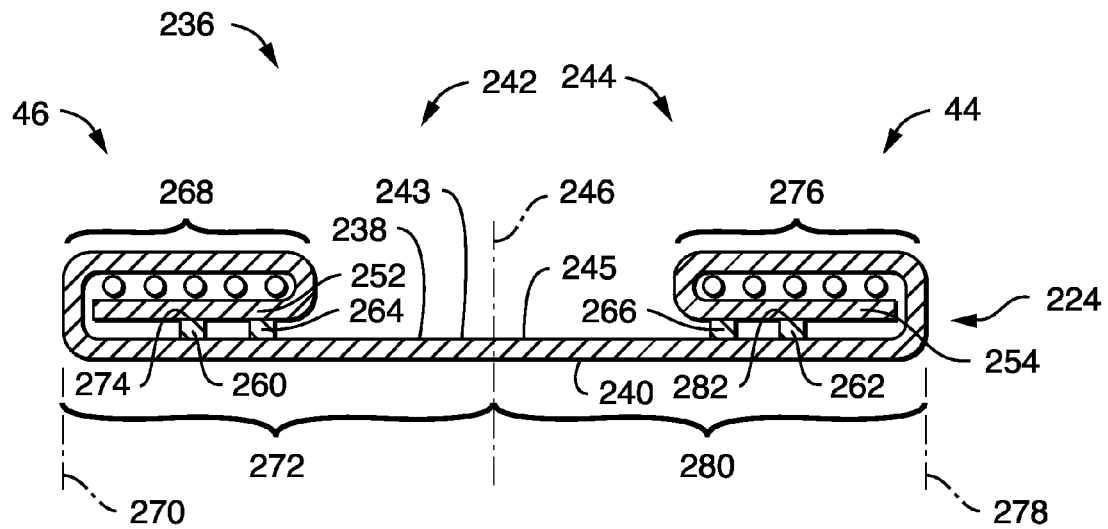
FIG. 12 is a cross-section view of a step of the method shown in FIG. 7.

Now referring to FIGS. 7, 11, and 12, the method 210 can further include a step 224. Step 224 can include folding a second portion 268 of the first half 242 of the substrate 236 at fold line 270 towards the centerline 246 and the proximal end 243 of the first half 242 of the substrate 236 onto a third portion 272 of the first half 242 of the substrate 236. Folding the second portion 268 of the first half 242 of the substrate 236 can be completed with a folding apparatus 269, such as, but not limited to, a folding board. The second portion 268 can be folded such that the first portion 252 is bonded to the third portion 272 at the adhesive 260 in substantially the middle 274 of the first portion 252. By doing so, the first portion 252 and the second portion 268 of the first half 242 of the substrate 236 can form the inner flap projection 78 and the outer flap projection 82 for the containment flap 46 to be of approximately equal length, as discussed above, shown in FIG. 4, and as will be discussed in further detail below. In folding the second portion 268 of the first half 242 of the substrate 236 onto the third portion 272 of the first half 242 of the substrate 236, the first portion 252 of the first half 242 of the substrate 236 can be secured to the third portion 272 with intermittent adhesive 264. Thus, the part of the first portion 252 that will form a part of the outer flap projection 82 can be secured to the third portion 272 with intermittent adhesive 264. The intermittent adhesive 264 can be registered and the first half 242 of the substrate 236 can be attached to the absorbent article 10 (as will be described below) such that the intermittent adhesive 264 is only present in a portion of the front waist region 12 and/or a portion of the rear waist region 14 of the absorbent article 10, but not in the crotch region 16, just as adhesives 98, 99 are shown as securing the outer flap projection 82 in FIGS. 2, 5, and 6. Alternatively and/or additionally to the use of adhesive 260 and intermittent adhesive 264, the first portion 252 can be secured to the third portion 272 via other bonding methods, including, but not limited to, pressure bonding or ultrasonic bonding the first portion 252 to the third portion 272.

Likewise, step 224 can include folding a second portion 276 of the second half 244 of the substrate 236 at fold line 278 towards the centerline 246 and the proximal end 245 of the second half 244 of the substrate 236 onto a third portion 280 of the second half 244 of the substrate 236. Folding the second portion 276 of the second half 244 of the substrate 236 can be accomplished with the folding apparatus 269. The second portion 276 can be folded such that the first portion 254 is bonded to the third portion 280 at the adhesive 262 in substantially the middle 282 of the first portion 254. In this manner, the first portion 254 and the second portion 276 of the second half 244 of the substrate 236 can form the inner flap projection 76 and the outer flap projection 80 of the containment flap 44 to be of approximately equal length, as discussed above, shown in FIG. 4, and as will be discussed in further detail below. In folding the second portion 276 of the second half 244 of the substrate 236 onto the third portion 280 of the second half 244 of the substrate 236, the first portion 254 of the second half 244 of the substrate can be bonded to the third portion 280 with intermittent adhesive 266. As a result, the first portion 254 can be secured to the third portion 280 with intermittent adhesive 266. Thus, the part of the first portion 254 that will form a part of the outer flap projection 80 can be secured to the third portion 280 with intermittent adhesive 266. The intermittent adhesive 266 can be registered and the second half 244 of the substrate 236 can be attached to the absorbent article 10 (as will be described below) such that the intermittent adhesive 266 is only present in a portion of the front waist region 12 and/or a portion of rear waist region 14 of the absorbent article, but not in the crotch region 16, just as adhesives 94, 95 are shown as securing the outer flap projection 80 in FIGS. 2, 5, and 6. Alternatively and/or additionally to the use of adhesive 262 and intermittent adhesive 266, the first portion 254 can be secured to the third portion 280 via other bonding methods, including, but not limited to, pressure bonding or ultrasonic bonding the first portion 254 to the third portion 280.

Figure 13:
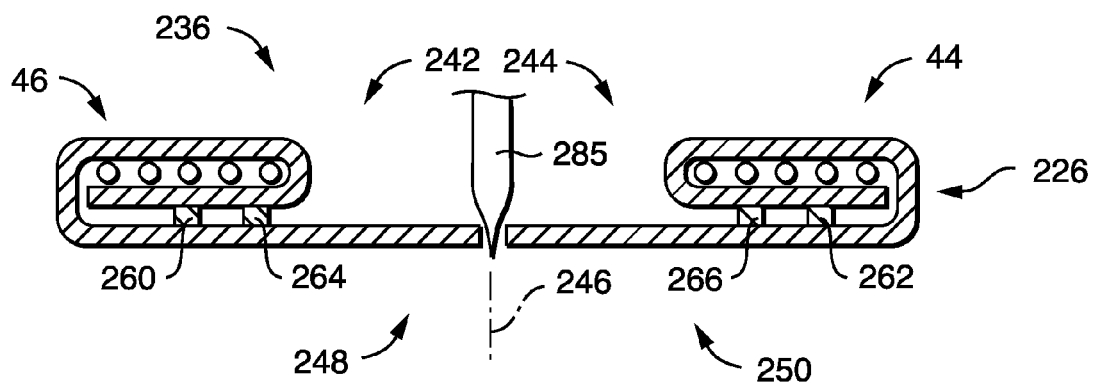
FIG. 13 is a cross-section view of a step of the method shown in FIG. 7.

Referring to FIGS. 7 and 13, step 226 of the method 210 can include slitting the substrate 236 at the centerline 246 to separate the first half 242 of the substrate 236 from the second half 244 of the substrate 236. A slitting apparatus 284 can slit the substrate 236, the slitting apparatus 284 being any of a variety of equipment that is capable of cutting a web of material into two webs, as is known by one of ordinary skill in the art. For example, the slitting apparatus can include a blade 285 as illustrated in FIG. 13. As previously noted, step 236 can be completed prior to step 214 if the substrate 236 is provided as a first half 242 and a second half 244 that are already separated from one another to form a first substrate and a second substrate. Alternatively, slitting the substrate 236 could be performed in various stages of the method 210 described herein for example, after step 214 and prior to step 216, after step 216 and prior to step 218, after step 218 and prior to step 220, after step 220 and prior to step 222, or after step 222 and prior to step 224.

Figure 14:
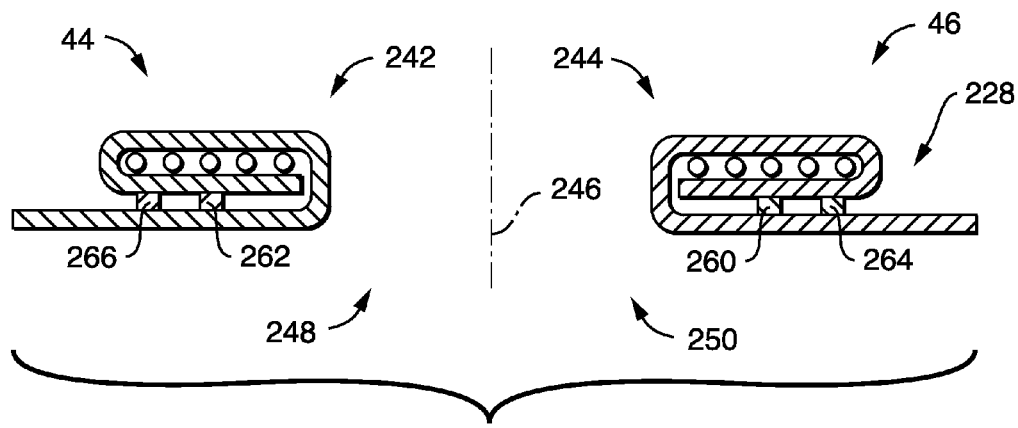
FIG. 14 is a cross-section view of a step of the method shown in FIG. 7.

Referring to FIGS. 7 and 14, step 228 includes moving the first half 242 of the substrate 236 from the first side 248 of the centerline 246 to the second side 250 of the centerline 246 and moving the second half 244 of the substrate 236 from the second side 250 of the centerline 246 to the first side 248 of the centerline 246. Reversing the orientation of the first half 242 of the substrate 236 and the second half 244 of the substrate 236 with respect to the centerline 246 can be accomplished with a web handling apparatus 286 as known by one of ordinary skill in the art. For example, the web handling apparatus 286 could be, but is not limited to, the location and angle of rollers that guide the first half 242 and the second half 244 of the substrate 236. Step 228 can alternatively be performed in the method 210 at any point after the first half 242 is separated from the second half 244 of the substrate 236, such as in step 226.

Figure 15:
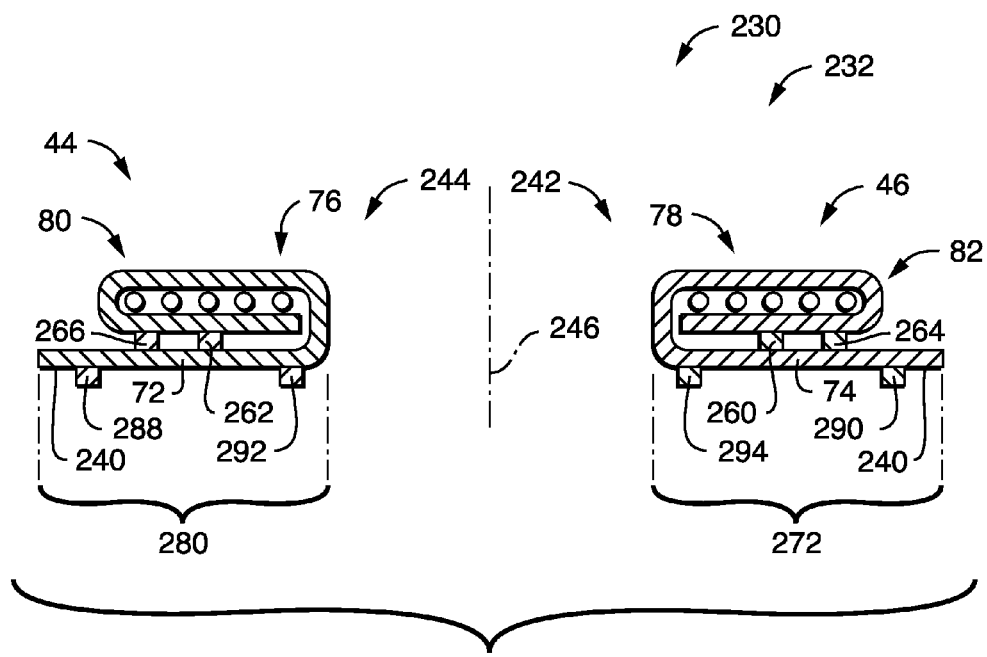
FIG. 15 is a cross-section view of a step of the method shown in FIG. 7.

FIGS. 7 and 15 illustrate step 230 of method 210. Step 230 can include applying adhesive 288 to the second surface 240 of the second half 244 of the substrate 236, in particular, in the third portion 280 of the second half 244 of the substrate 236. Step 230 can also include applying adhesive 290 to the second surface 240 of the first half 242 of the substrate 236, in the third portion 272 of the first half 242 of the substrate 236. The adhesives 288 and 290 can be applied by an adhesive applicator 291, which can be similar to the adhesive applicator 261 discussed above. The portion of the first half 242 of the substrate 236 extending between the adhesive 260 (applied in step 220) and the adhesive 290 (applied in step 230) can form the stem 74 of the containment flap 46. Additionally, the portion of the second half 244 of the substrate 236 extending between the adhesive 262 (applied in step 220) and the adhesive 288 (applied in step 230) can form the stem 72 of the containment flap 44.

Step 232 can include applying an intermittent adhesive 292 to the second surface 240 of the second half 244 of the substrate 236. Step 232 can also include applying intermittent adhesive 294 to the second surface 240 of the first half 242 of the substrate 236. The intermittent adhesives 292, 294 can be applied by the adhesive applicator 291 or by a different adhesive applicator (not shown). The intermittent adhesives 292, 294 can be applied to the second surface 240 of the first half 242 and the second half 244 of the substrate 236 at the same time the adhesives 288, 290 are applied, however, the method 210 is not limited to such a configuration. As illustrated in FIG. 15, the intermittent adhesive 292 can be applied to the second surface 240 of the second half 244 of the substrate 236 closer to the centerline 246 than the adhesive 288. Similarly, the intermittent adhesive 294 can be applied to the second surface 240 of the first half 242 of the substrate 236 closer to the centerline 246 than the adhesive 290. The intermittent adhesives 292 and 294 can be registered such that when the first half 242 and the second half 244 of the substrate is bonded to the absorbent article 10 (as will be discussed below), the intermittent adhesives 292, 294 are only present in the front waist region 12 and the rear waist region 14 of the absorbent article 10. Of course, step 232 could be performed at an earlier stage of method 210 or not form a step of the method 210.

With reference to FIGS. 7 and 15, step 234 can include bonding the second half 244 of the substrate 236 to the absorbent article 10 at the adhesive 288 to form the first containment flap 44 and bonding the first half 242 of the substrate 236 to the absorbent article 10 at the adhesive 290 to form the second containment flap 46, as illustrated in the absorbent article 10 in FIGS. 1-6 and as described above. The first half 242 and the second half 244 of the substrate 236 can be bonded to the body facing liner 28 and/or the backsheet 26, laterally inward of the longitudinal side edges 20, 18, respectively, and laterally inward from the elasticized leg cuffs 59, 57, respectively. The bonding can be completed by employing a bonding apparatus 296 as is known in the art. In one embodiment, the bonding apparatus 296 can be a pair of rollers that direct the first half 242 and the second half 244 of the substrate in contact with the body facing liner 28, such that the adhesives 288, 290 can complete the bond with the body facing liner 28 to form the containment flaps 44, 46 on the absorbent article 10. In doing so, the intermittent adhesives 292, 294 can also bond the second surface 240 of the second half 244 of the substrate 236 in the third portion 280 and the first half 242 of the substrate 236 in the third portion 272, respectively, to the body facing liner 28 as well, just as adhesives 92, 93, 96, and 97 are shown as intermittently bonding the inner flap projections 76, 78 to the body facing liner 28 in FIGS. 2 and 4-6. Thus, the third portion 280 of the second half 244 of the substrate 236 that forms a part of the inner flap projection 76 can be secured to the body facing liner 28 with intermittent adhesive 292 in the front region 12 and the rear region 14 of the absorbent article 10, but not in the crotch region 16. And, the third portion 272 of the first half 242 of the substrate 236 that forms a part of the inner flap projection 76 can be secured to the body facing liner 28 with intermittent adhesive 294 in the front region 12 and the rear region 14 of the absorbent article 10, but not in the crotch region 16.

Alternatively and/or additionally to the use of adhesives 288, 290 and intermittent adhesives 292 and 294, the first half 242 and the second half 244 of the substrate 236 can be secured to the body facing liner 28 or the backsheet 26 to form the containment flaps 44, 46 with other bonding methods known in the art, including, but not limited to, pressure bonding or ultrasonically bonding the first half 242 and the second half 244 of the substrate 236 to the body facing liner 28 or the backsheet 26.

In bonding the first half 242 and the second half 244 of the substrate 236 to the absorbent article 10 to form the containment flaps 46, 44, the intermittent adhesives 264, 266, 292, 294 can be registered and the first half 242 and the second half 244 of the substrate 236 can be attached to the body facing liner 28 (or alternatively the backsheet 26) such that one or more of the intermittent adhesives 264, 266, 292, 294 are present in at least a portion of the front waist region 12 and/or the rear waist region 14, but not in the crotch region 16 of the absorbent article 10. The application of the intermittent adhesives 264, 266 to the first half 242 and the second half 244 of the substrate 236, respectively, can secure the outer flap projections 82, 80 of the containment flaps 46, 44, respectively, in the front waist region 12 and/or the rear waist region 14, but not in the crotch region 16, of the absorbent article 10, as previously described and as shown in FIGS. 2 and 4-6 (with adhesives 94 and 95 being comparable to intermittent adhesive 266 and adhesives 98 and 99 being comparable to intermittent adhesive 264). Furthermore, the application of the intermittent adhesives 292 and 294 to the second half 244 and the first half 242 of the substrate 236, respectively, can secure the inner flap projections 76, 78 of the containment flaps 44, 46, respectively, as previously described and as shown in FIGS. 2 and 4-6 (with adhesives 92 and 93 being comparable to intermittent adhesive 292 and adhesives 96 and 97 being comparable to intermittent adhesive 294).

As an alternative or an addition to intermittent adhesives 264, 266, 292, 294, the inner flap projections 76, 78 and the outer flap projections 80, 82 could be secured in the front waist region 12 and/or the rear waist region 14 using other bonding methods or structure. For example, the inner flap projections 76, 78 could be secured in the front waist region 12 and/or the rear waist region 14 by being bonded to the body facing liner 28 by an intermittent pressure bond or an intermittent ultrasonic bond, or the like. Additionally, the outer flap projections 80, 82 could be secured in the front waist region 12 and/or the rear waist region 14 by being bonded to the stem 72, 74 by a pressure bond or an ultrasonic bond, or the like.

Leg Elastics:

Leg elastic members 56, 58 can be secured to the backsheet 26, such as by being bonded thereto by laminate adhesive, generally laterally inward of the longitudinal side edges, 18 and 20, of the absorbent article 10. The leg elastic members 56, 58 can form elasticized leg cuffs 57, 59, respectively, that further help to contain body exudates. In an embodiment, the leg elastic members 56, 58 may be disposed between the inner layer 62 and outer layer 60 of the backsheet 26 or between other layers of the absorbent article 10. The elasticized leg cuff 57 can be positioned laterally outward of the stem 72 of the containment flap 44 and the elasticized leg cuff 59 can be positioned laterally outward of the stem 74 of the containment flap 46. The leg elastic members 56, 58 can be a single elastic member as illustrated in the figures herein, or each leg elastic member 56, 58 can include more than one elastic member. A wide variety of elastic materials may be used for the leg elastic members 56, 58. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 10 can include a fastener system. The fastener system can include one or more back fasteners 130 and one or more front fasteners 132. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 130 can include one or more materials bonded together to form a composite ear as is known in the art. For example, the composite fastener may be composed of a stretch component 134, a nonwoven carrier or hook base 136, and a fastening component 138.

Waist Elastic Members:

In an embodiment, the absorbent article 10 can have waist elastic members, 52 and 54, which can be formed of any suitable elastic material. The waist elastic member 52 can be in a rear waist region 12 of the absorbent article 10 and the waist elastic member 54 can be in a front waist region 14 of the absorbent article. Suitable elastic materials for the waist elastic members 52, 54 can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 52 and 54, may be omitted from the absorbent article 10 without departing from the scope of this disclosure.

Figure 16:
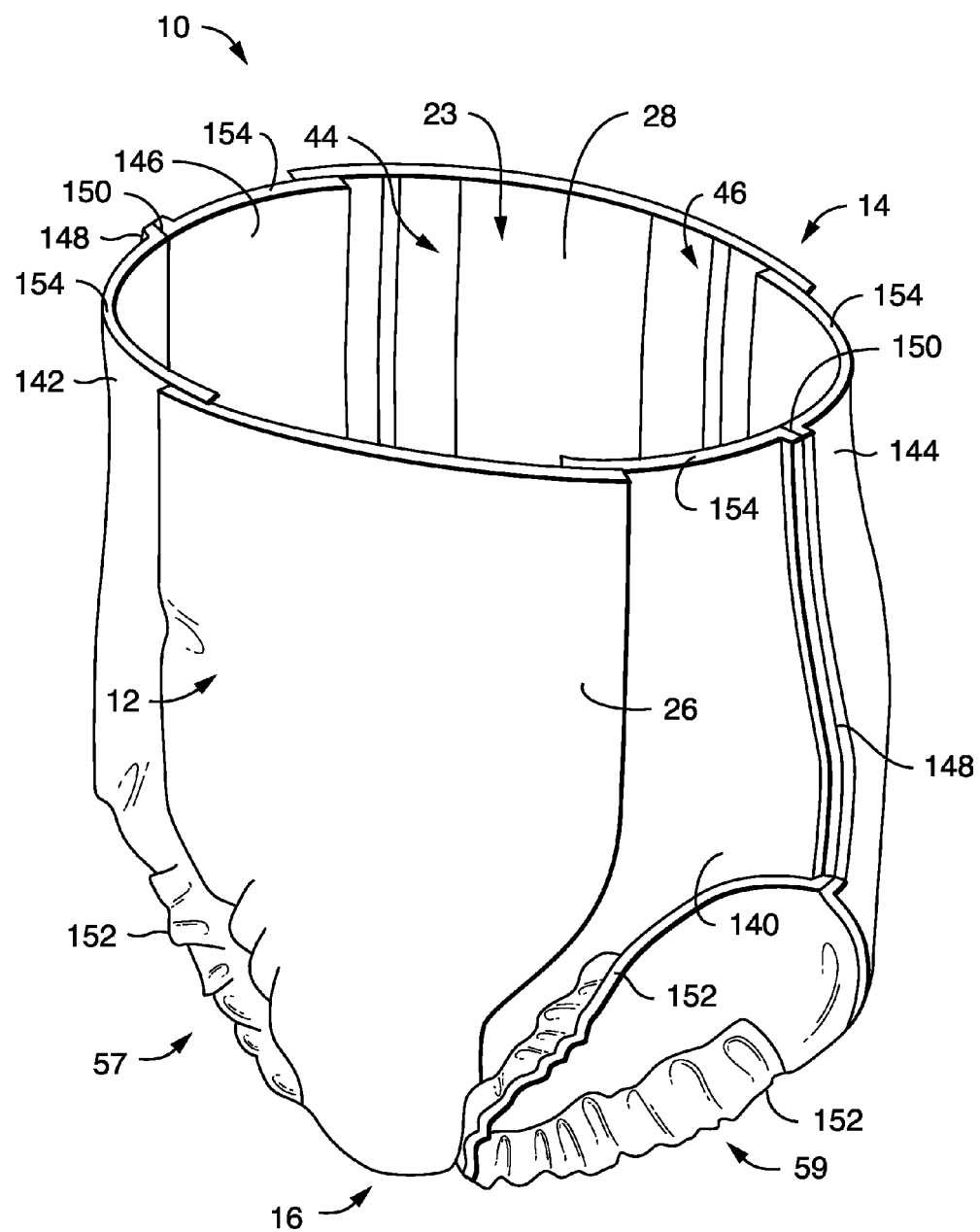
FIG. 16 is a perspective view of an exemplary embodiment of an absorbent article, such as a training pant, in a fastened condition.

Side Panels:

As illustrated in FIG. 16, in an embodiment in which the absorbent article 10 can be a training pant, youth pant, diaper pant, or adult absorbent pant, the absorbent article 10 may have front side panels, 140 and 142, and rear side panels, 144 and 146. FIG. 16 provides a non-limiting illustration of an absorbent article 10 that can have side panels, such as front side panels, 140 and 142, and rear side panels, 144 and 146. The front side panels 140 and 142 and the rear side panels 144 and 146 of the absorbent article 10 can be bonded to the absorbent article 10 in the respective front and back waist regions, 12 and 14, and can extend outwardly beyond the longitudinal side edges, 18 and 20, of the absorbent article 10. In an example, the front side panels, 140 and 142, can be bonded to the inner layer 62 of the backsheet 26, such as being bonded thereto by adhesive, by pressure bonding, by thermal bonding or by ultrasonic bonding. These front side panels, 140 and 142, may also be bonded to the outer layer 60 of the backsheet 26, such as by being bonded thereto by adhesive, by pressure bonding, by thermal bonding, or by ultrasonic bonding. The back side panels, 144 and 146, may be secured to the outer and inner layers, 60 and 62 respectively, of the backsheet 26 at the back waist region 14 of the absorbent article 10 in substantially the same manner as the front side panels, 140 and 142. Alternatively, the front side panels, 140 and 142, and the back side panels, 144 and 146, may be formed integrally with the absorbent article 10, such as by being formed integrally with the backsheet 26, the body facing liner 28, or other layers of the absorbent article 10. As illustrated in FIG. 16, the absorbent article 10 can include the containment flaps 44, 46 as discussed above. The containment flaps 44, 46 can be bonded to the body facing liner 28.

For improved fit and appearance, the front side panels, 140 and 142, and the back side panels, 144 and 146, can suitably have an average length measured parallel to the longitudinal axis 29 of the absorbent article 10 that is about 20 percent or greater, and more suitably about 25 percent or greater, of the overall length of the absorbent article 10, also measured parallel to the longitudinal axis 29. For example, absorbent articles 10 having an overall length of about 54 centimeters, the front side panels, 140 and 142, and the back side panels, 144 and 146, suitably have an average length of about 10 centimeters or greater, and more suitably have an average length of about 15 centimeters. Each of the front side panels, 140 and 142, and back side panels, 144 and 146, can be constructed of one or more individual, distinct pieces of material. For example, each front side panel, 140 and 142, and back side panel, 144 and 146, can include first and second side panel portions (not shown) joined at a seam (not shown), with at least one of the portions including an elastomeric material. Alternatively, each individual front side panel, 140 and 142, and back side panel, 144 and 146, can be constructed of a single piece of material folded over upon itself along an intermediate fold line (not shown).

The front side panels, 140 and 142, and back side panels, 144 and 146, can each have an outer edge 148 spaced laterally from the engagement seam 150, a leg end edge 152 disposed toward the longitudinal center of the absorbent article 10, and a waist end edge 154 disposed toward a longitudinal end of the absorbent article 10. The leg end edge 152 and waist end edge 154 can extend from the longitudinal side edges, 18 and 20, of the absorbent article 10 to the outer edges 190. The leg end edges 152 of the front side panels, 140 and 142, and back side panels, 144 and 146, can form part of the longitudinal side edges, 18 and 20, of the absorbent article 10. The leg end edges 152 of the illustrated absorbent article 10 can be curved and/or angled relative to the transverse axis to provide a better fit around the wearer's legs. However, it is understood that only one of the leg end edges 152 can be curved or angled, such as the leg end edge 152 of the back waist region 14, or neither of the leg end edges 152 can be curved or angled, without departing from the scope of this disclosure. The waist end edges 154 can be parallel to the transverse axis. The waist end edges 154 of the front side panels, 140 and 142, can form part of the front waist edge 22 of the absorbent article 10, and the waist end edges 154 of the back side panels, 144 and 146, can form part of the back waist edge 24 of the absorbent article 10.

The front side panels, 140 and 142, and back side panels, 144 and 146, can include an elastic material capable of stretching laterally. Suitable elastic materials, as well as one described process for incorporating elastic front side panels, 140 and 142, and back side panels, 144 and 146, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987, in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 140 and 142, and back side panels, 144 and 146, may include other woven or non-woven materials, such as those described above as being suitable for the backsheet 26, mechanically pre-strained composites, or stretchable but inelastic materials.

Figure 17:
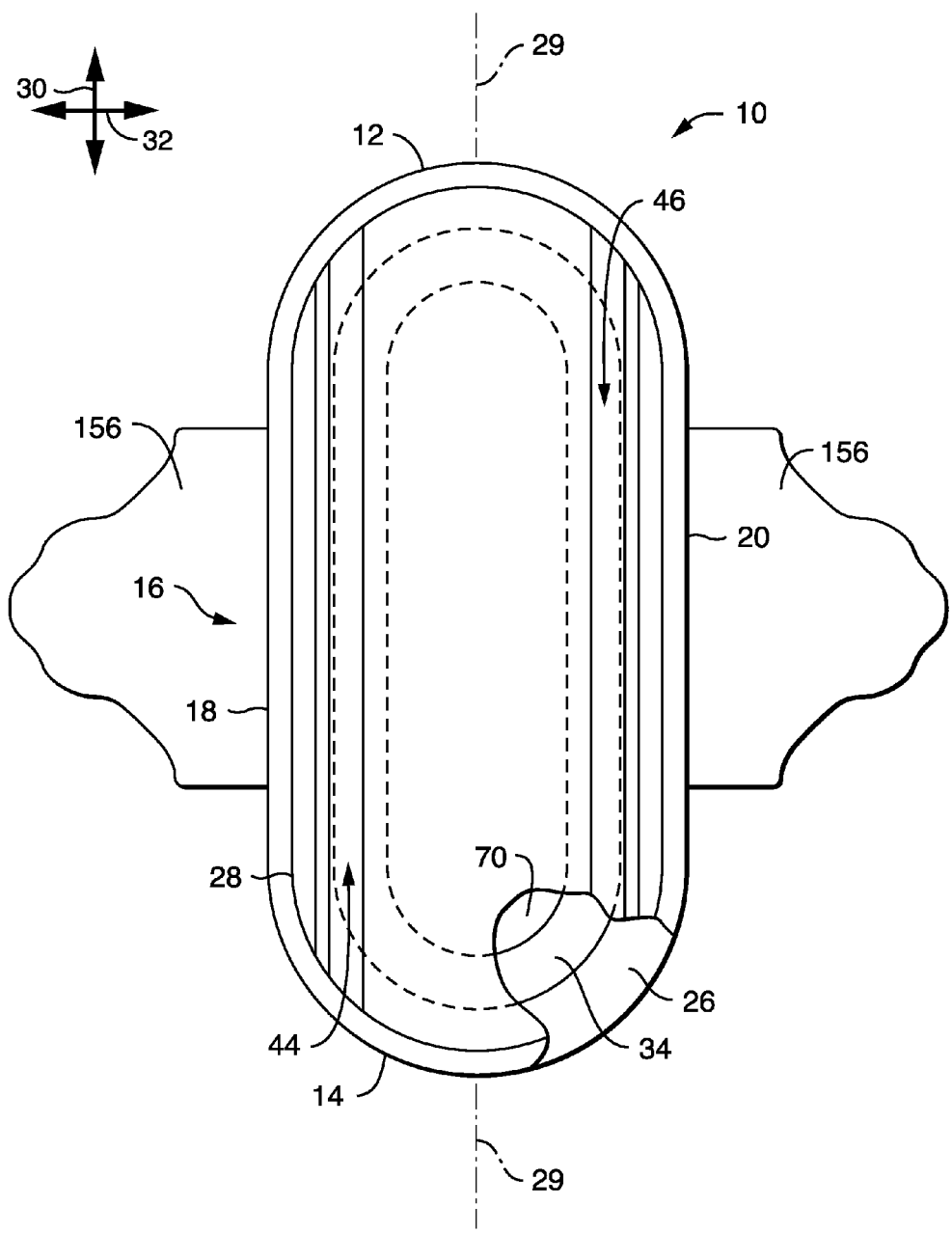
FIG. 17 is a top plan view of an exemplary embodiment of an absorbent article, such as a feminine hygiene product.

Feminine Hygiene Product:

FIG. 17 provides a non-limiting illustration of an absorbent article 10 in the form of a feminine hygiene product such as a menstrual pad or feminine adult incontinence product. The absorbent article 10 can have a lengthwise, longitudinal direction 30 and a transverse, lateral direction 32. Additionally, the absorbent article 10 can include first and second longitudinally opposed front and rear regions, 12 and 14, and an intermediate region (or crotch region) 16, located between the end regions, 12 and 14. The absorbent article 10 can have first and second longitudinal side edges, 18 and 20, which can be the longitudinal sides of the elongated absorbent article 10. The longitudinal side edges, 18 and 20, can be contoured to match the shape of the absorbent article 10. The absorbent article 10 can have any desired shape such as, for example, a dog bone shape, a race track shape, an hourglass shape, or the like. Additionally, the absorbent article 10 can be substantially longitudinally symmetric, or may be longitudinally asymmetric, as desired.

As representatively shown, the longitudinal dimension of the absorbent article 10 can be relatively larger than the transverse lateral dimension of the absorbent article 10. Configurations of the absorbent article 10 can include a body facing liner 28 and a backsheet 26, such as described herein. An absorbent body 34, such as described herein, can be positioned between the body facing liner 28 and the backsheet 26. As representatively shown, for example, the peripheries of the body facing liner 28 and the backsheet 26 can be substantially entirely coterminous or the peripheries of the body facing material 28 and the backsheet 26 can be partially or entirely non-coterminous. In an embodiment, the absorbent article 10 can include an acquisition layer 70 such as described herein. In an embodiment, the absorbent article 10 can include the containment flaps 44, 46 as described herein. The containment flaps 44, 46 can be bonded to the body facing liner 28.

In an embodiment in which the absorbent article 10 can be a feminine hygiene product, the absorbent article 10 can include laterally extending wing portions 156 that can be integrally connected to the side edges, 18 and 20, of the absorbent article 10 in the intermediate region 16 of the absorbent article 10. For example, the wing portions 156 may be separately provided members that are subsequently attached or otherwise operatively joined to the intermediate region 16 of the absorbent article 10. In other configurations, the wing portions 156 may be unitarily formed with one or more components of the absorbent article 10. As an example, a wing portion 156 may be formed from a corresponding, operative extension of the body facing liner 28, the backsheet 26, and combinations thereof.

The wing portions 156 can have an appointed storage position (not shown) in which the wing portions 156 are directed generally inwardly toward the longitudinal axis 29. In various embodiments, the wing portion 156 that is connected to one side edge, such as side edge 18, may have sufficient cross-directional length to extend and continue past the axis 29 to approach the laterally opposite side edge 20 of the absorbent article 10. The storage position of the wing portions 156 can ordinarily represent an arrangement observed when the absorbent article 10 is first removed from a wrapper or packaging. Prior to placing the absorbent article 10, such as the feminine hygiene product, into a bodyside of an undergarment prior to use, the wing portions 156 can be selectively arranged to extend laterally from the side edges, 18 and 20, of the absorbent article 10 intermediate region 16. After placing the absorbent article 10 into the undergarment, the wing portions 156 can be operatively wrapped and secured around the side edges 18, 20 of the undergarment to help hold the absorbent article 10 in place, in a manner well known in the art.

The wing portions 156 can have any operative construction and can include a layer of any operative material. Additionally, each wing portion 156 can comprise a composite material. For example, the wing portions 156 can include a spunbond fabric material, a bicomponent spunbond material, a necked spunbond material, a neck-stretched-bonded laminate (NBL) material, a meltblown fabric material, a bonded carded web, a thermal bonded carded web, a through-air bonded carded web, or the like, as well as combinations thereof.

Each wing portion 156 can include a panel-fastener component (not shown) which can be operatively joined to an appointed engagement surface of its associated wing portion 156. The panel-fastener component can include a system of interengaging mechanical fasteners, a system of adhesive fasteners, or the like, as well as combinations thereof. In an embodiment, either or both wing portions 156 can include a panel-fastener system which incorporates an operative adhesive. The adhesive may be a solvent based adhesive, a hot melt adhesive, a pressure-sensitive adhesive, or the like, as well as combinations thereof.

In an embodiment, a garment attachment mechanism (not shown), such as a garment attachment adhesive, can be distributed onto the garment side of the absorbent article 10. In an embodiment, the garment adhesive can be distributed over the garment side of the absorbent article 10 of the backsheet 26, and one or more layers or sheets of release material can be removably placed over the garment adhesive for storage prior to use. In an embodiment, the garment attachment mechanism can include an operative component of a mechanical fastening system. In such an embodiment, the garment attachment mechanism can include an operative component of a hook-and-loop type of fastening system.

Decolorizing Composition:

In an embodiment, a chemical treatment may be employed to alter the color of bodily exudates captured by the absorbent article 10. In an embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al., which is incorporated herein in its entirety by reference thereto. Non-limiting examples of such surfactants include Pluronic® surfactants (tri-block copolymer surfactant), inorganic salts that contain a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($Li^+$), ammonium ($NH_4^+$), etc. Alkali metal cations are also beneficial. Some examples of salts formed from such ions include, but are not limited to, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may also be effective in facilitating physical separation of red blood cells. For example, a mixture of disodium sulfate ($Na_2SO_4$) and monopotassium phosphate ($KH_2PO_4$) may be employed.

Besides agglutinating agents, the decolorizing composition may alter the chemical structure of hemoglobin to change its color. Examples of such compositions are described in U.S. Patent Application Publication No. 2009/0062764 to MacDonald, et al., which is incorporated herein in its entirety by reference thereto. In an embodiment, the composition can include an oxidizing agent that can be generally capable of oxidizing hemoglobin or other substances responsible for unwanted color of the bodily exudates. Some examples of oxidizing agents include, but are not limited to, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, strontium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassium dipersulphate, and potassium persulphate); and so forth. Other suitable oxidizing agents include, but are not limited to omega-3 and -6 fatty acids, such as linoleic acids, α-linoleic acid, arachidonic acid, eicosapentaenoic acid, docosahexaenoic acid, eicosadienoinc acid, eicosatrienoic acid, etc.

The decolorizing composition may be applied to any liquid permeable layer of the absorbent article 10 where it can contact aqueous fluids exuded by the body, such as, for example, menses, such as the body facing liner 28, acquisition layer 70, fluid transfer layer 68, absorbent body 34, backsheet 26, and combinations thereof. In an embodiment, the decolorizing composition may be applied to only a portion of the surface of the layer(s) to which it is applied to ensure that the layer(s) is still capable of retaining sufficient absorbent properties. In an embodiment, it may be desired that the decolorizing composition is positioned closer to the absorbent body 40. In an embodiment, an additional layer (not shown) may be employed in the absorbent article 10 and may be applied with the decolorizing composition that is in contact with the absorbent body 40. The additional layer may be formed from a variety of different porous materials, such as a perforated film, nonwoven web (e.g., cellulosic web, spunbond web, meltblown web, etc.), foams, etc. In an embodiment, the additional layer may be in the form of a hollow enclosure (e.g., sachet, bag, etc.) that is folded so that it partially or completely surrounds the absorbent body 40.

The decolorizing composition may be disposed within this enclosure so that it remains sealed therein prior to use.

Packaging Fold Lines of the Absorbent Article

Any of the absorbent articles 10 including the containment flaps 44, 46 discussed above can be folded to reduce the length and width of the absorbent article 10 for packaging purposes. Equipment used to fold the absorbent articles 10 is known to one having ordinary skill in the art.

Figure 18:
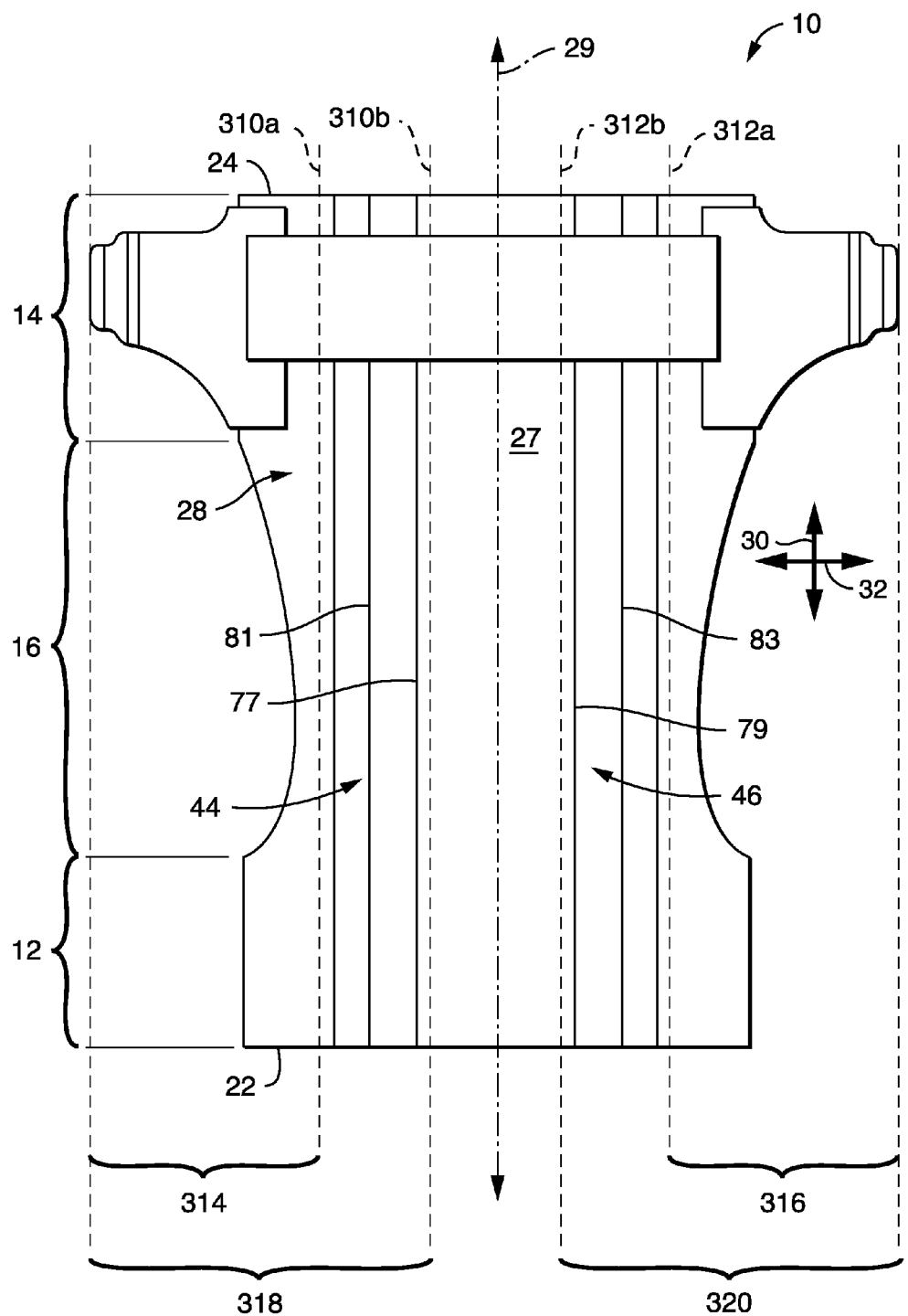
FIG. 18 is a top plan view of the absorbent article of FIG. 1 in a stretched, laid flat condition and illustrating potential locations for packaging fold lines.
Figure 19:
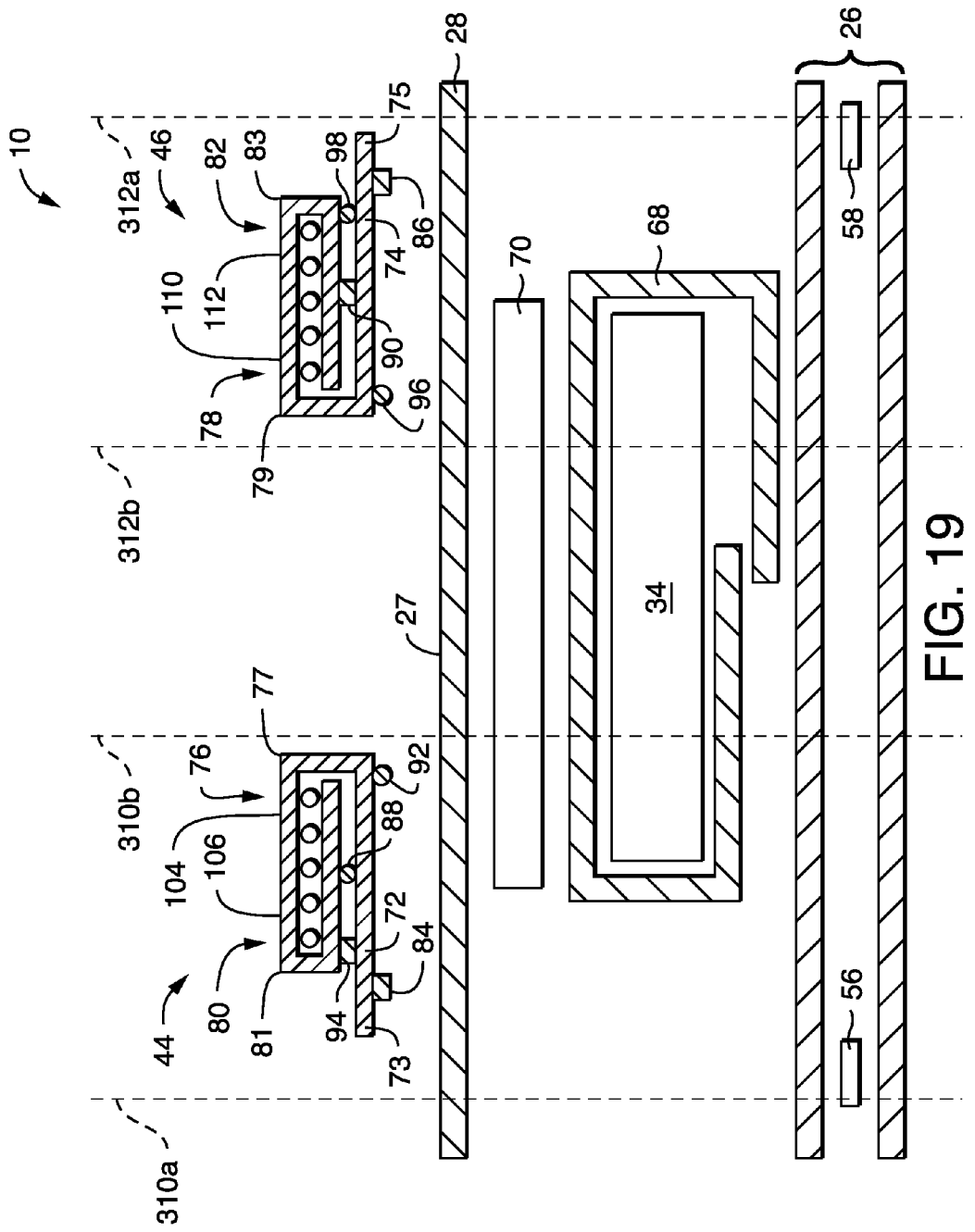
FIG. 19 is a cross-section, exploded view of a crotch region of the absorbent article of FIG. 18.

With respect to FIGS. 18-25, the selective location of packaging fold lines 310a, 310b, 310c, 310d, 310e, 312a, 312b, 312c, 312d, and 312e on absorbent article 10 as well as their effects on the containment flaps 44, 46 when the absorbent article 10 is unfolded and placed in a relaxed condition will now be discussed. Turning first to FIG. 18, a top plan view of an absorbent article 10, such as a diaper, as shown in FIG. 1 is illustrated in a stretched, laid flat configuration. The absorbent article 10 includes the containment flaps 44, 46 bonded to the body facing liner 28, as previously discussed. FIGS. 18 and 19 illustrates four fold lines 310a, 310b, 312a, and 312b that provide multiple options for providing packaging folds in the absorbent article 10. Each of the four fold lines 310a, 310b, 312a, and 312b can be substantially parallel to the longitudinal axis 29 of the absorbent article 10 and can extend from the front end edge 22 to the rear end edge 24.

First, the absorbent article 10 can include fold lines 310a and 312a. Fold line 310a can be on the same side of the longitudinal axis 29 as the containment flap 44 and the fold line 312a can be on the same side of the longitudinal axis 29 as the containment flap 46. The fold line 310a can be located such that a distal edge 81 of the outer flap projection 80 on the containment flap 44 is positioned laterally inside of the fold line 310a. Or, in other words, the distal edge 81 of the outer flap projection 80 on the containment flap 44 can be closer to the longitudinal axis 29 than the fold line 310a. Similarly, fold line 312a can be located such that a distal edge 83 of the outer flap projection 82 on the containment flap 46 is positioned laterally inside of the fold line 312a, and thus, the distal edge 83 can be closer to the longitudinal axis 29 than the fold line 312a. The absorbent article 10 can be folded along lines 310a and 312a by folding a longitudinal portion 314 of the absorbent article 10 laterally outside of the folding line 310a towards the longitudinal axis 29 and on top of the body facing surface 27 of the body facing liner 28 and folding a longitudinal portion 316 of the absorbent article 10 laterally outside of the folding line 312a towards the longitudinal axis 29 and on top of the body facing surface 27 of the body facing liner 28, as depicted in FIG. 18.

By providing the fold lines 310a, 312a laterally outside of the distal edges 81, 83 of the outer flap projections 80, 82, respectively, the shape of the inner flap projections 76, 78 and the outer flap projections 80, 82 of the containment flaps 44, 46, respectively, can be maintained when the absorbent article is folded into a packaging position along lines 310a, 312a. As noted above, maintaining the upper surfaces 104, 110 of the inner flap projections 76, 78, respectively, and the upper surfaces 106, 112 of the outer flap projections 80, 82, respectively, to be level with one another can provide increased contact area with the wearer's skin, which, in one embodiment, can help provide beneficial gasketing properties against body exudates.

Although fold lines 310a and 312a are shown as being laterally outward from the stem 72, 74 and foot portions 73, 75 of the containment flaps 44, 46, respectively, it is contemplated that fold lines 310a and 312a can extend through the foot portions 73, 75 and/or the stems 72, 74 of the containment flaps 44, 46, respectively, and yet still achieve the desired properties noted above.

Second, the absorbent article 10 can alternatively include fold lines 310b and 312b. Fold line 310b can be on the same side of the longitudinal axis 29 as the containment flap 44 and the fold line 312b can be on the same side of the longitudinal axis 29 as the containment flap 46. The fold line 310b can be located such that a distal edge 77 of the inner flap projection 76 on the containment flap 44 is positioned laterally outside of the fold line 310b. Stated in another way, the distal edge 77 of the inner flap projection 76 can be farther from the longitudinal axis 29 than the fold line 310b. Similarly, fold line 312b can be located such that a distal edge 79 of the inner flap projection 78 of the containment flap 46 is positioned laterally outside of the fold line 312b. Thus, the distal edge 79 of the inner flap projection 78 can be farther from the longitudinal axis 29 than the fold line 312b. The absorbent article 10 can be folded along lines 310b and 312b by folding a longitudinal portion 316 of the absorbent article 10 laterally outside of the folding line 310b towards the longitudinal axis 29 and on top of the body facing surface 27 of the body facing liner 28 and folding a longitudinal portion 320 of the absorbent article 10 laterally outside of the folding line 312b towards the longitudinal axis 29 and on top of the body facing surface 27 of the body facing liner 28, as depicted in FIG. 18.

Similar to the discussion above with respect to fold lines 310a, 312a, the selective positioning of fold lines 310b and 312b can maintain the integrity and the shape of the inner flap projections 76, 78 and the outer flap projections 80, 82 of the containment flaps 44, 46, respectively, which can provide increased contact area with the wearer's skin, as noted above. Of course, depending on the orientation of the stems 72, 74 and the foot portions 73, 75 of the containment flaps 44, 46, respectively, the fold lines 310b, 312b could extend through the stems 72, 74 and/or the foot portions 73, 75 of the containment flaps 44, 46, respectively, yet have the distal edges 77, 79 of the containment flaps 44, 46, still be laterally outside of the fold lines 310b, 312b, respectively. As a result, the same benefits noted above regarding maintaining the upper surfaces 104, 110 of the inner flap projections 76, 78 and the upper surfaces 106, 112 of the outer flap projections 80, 82, respectively, to be level with one another can still be realized in this alternative folding configuration.

Additionally, it is within the scope of this disclosure that the absorbent article 10 could be folded with packaging fold lines 310a and 312b or packaging fold lines 310b and 312a. Depending on considerations such as the desired folded size of the absorbent article 10 and the size of the absorbent article 10 in an unfolded condition, one or more of these folding combinations may be desirable. The benefits of having one of the distal edges 81, 83 of the outer flap projections 80, 82 laterally inside of one of the packaging fold lines 310a or 312a and one of the distal edges 77, 79 of the inner flap projections 76, 78 laterally outside one of the packaging fold lines 310b or 312b still provides the benefits for the containment flaps 44, 46 noted above. Additionally, it is also within the scope of this disclosure that the absorbent article 10 could be folded with just a single packaging fold line 310a, 310b, 312a, or 312b in the location shown in FIG. 18, with another packaging fold line extending through the absorbent article 10 at a location not shown for packaging fold lines 310a, 310b, 312a, or 312b to achieve the benefits noted above for at least one of the containment flaps 44, 46.

Furthermore, the securing of at least a portion of the inner flap projections 76, 78 and/or the outer flap projections 80, 82 of the containment flaps 44, 46, respectively, in the front end region 12 and/or the rear end region 14 as previously discussed can also provide additional benefits in helping the inner flap projections 76, 78 and the outer flap projections 80, 82 remain level in the crotch region 16 after the absorbent article 10 is unfolded by a user or wearer and applied to the wearer. As one example, if the absorbent article 10 is folded such that portion 314 is folded onto the body facing liner 28 at fold line 310a, a portion of the outer flap projection 80 of the containment flap 44 may be susceptible to unintentionally folding on top of the inner flap projection 76. Similarly, if the longitudinal portion 316 is folded onto the body facing liner 28 at fold line 312a, a portion of the outer flap projection 82 of the containment flap 46 may be susceptible to unintentionally folding on top of the inner flap projection 78. Because the absorbent article 10 may remain in this folded nature for some time, the unintended folding of portions of the outer flap projections 80, 82 on top of the inner flap projections 76, 78, respectively, may result in the upper surfaces 104, 110 of the containment flap 44 and the upper surfaces 106, 112 of the containment flap 46 being substantially non-uniform with one another and substantially non-uniform along a length of the absorbent article 10 in the longitudinal direction 30, which may lead to less than desirable gasketing of body exudates by the containment flaps 44, 46. Although some manipulation of the upper surfaces 104, 106 and 110, 112 of the containment flaps 44, 46, respectively, could be desirable in certain circumstances, as will be discussed below, it is believed that such manipulation of the containment flaps 44, 46 should be controlled in order to provide intended benefits as opposed to potential drawbacks for the gasketing properties of the containment flaps 44, 46.

Figure 20:
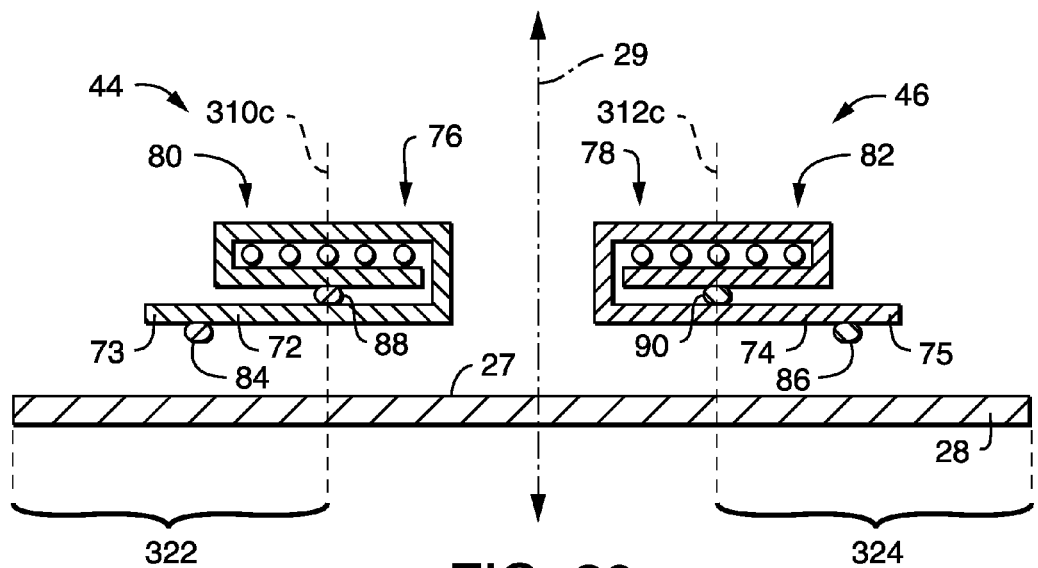
FIG. 20 is a cross-section, exploded view of the body facing liner and containment flaps in the crotch region of the absorbent article of FIG. 1 in a stretched, laid flat condition and illustrating alternative packaging fold lines.
Figure 21:
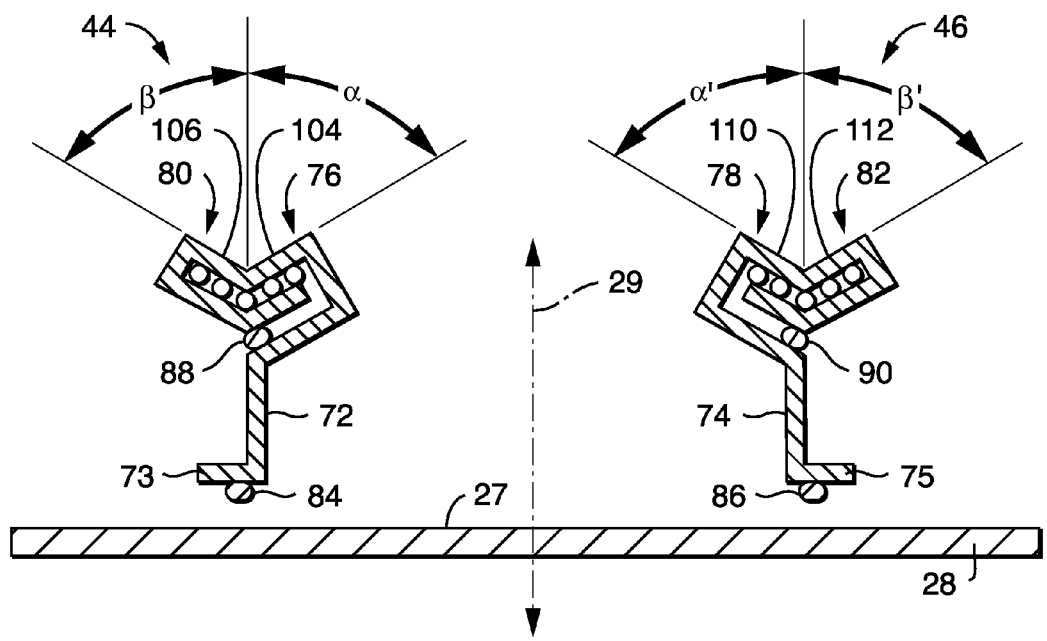
FIG. 21 is a cross-section, exploded view of a crotch region of the absorbent article having the packaging fold lines of FIG. 20 when the absorbent article is in a relaxed, unfolded condition.
Figure 22:
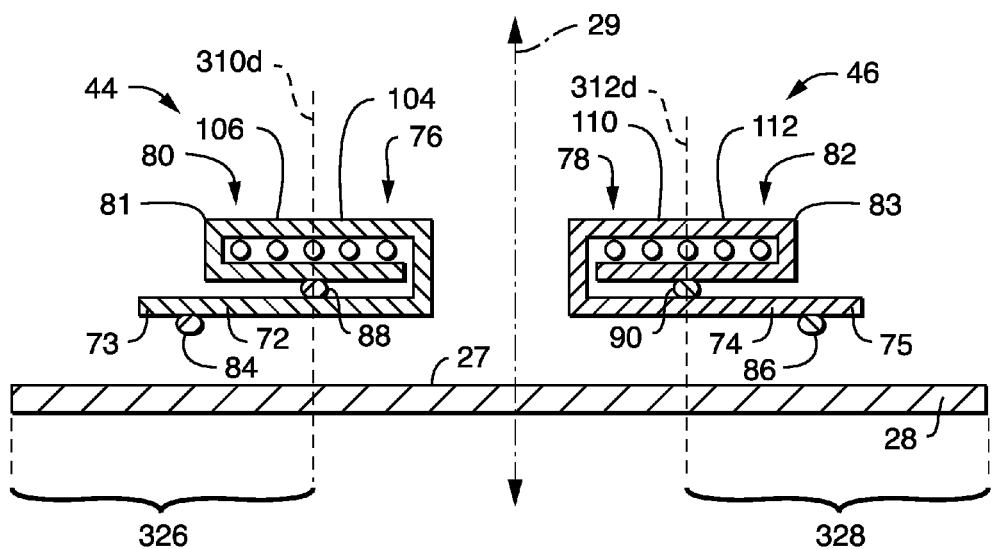
FIG. 22 is a cross-section, exploded view of the body facing liner and containment flaps in the crotch region of the absorbent article of FIG. 1 in a stretched, laid flat condition and illustrating alternative packaging fold lines.
Figure 23:
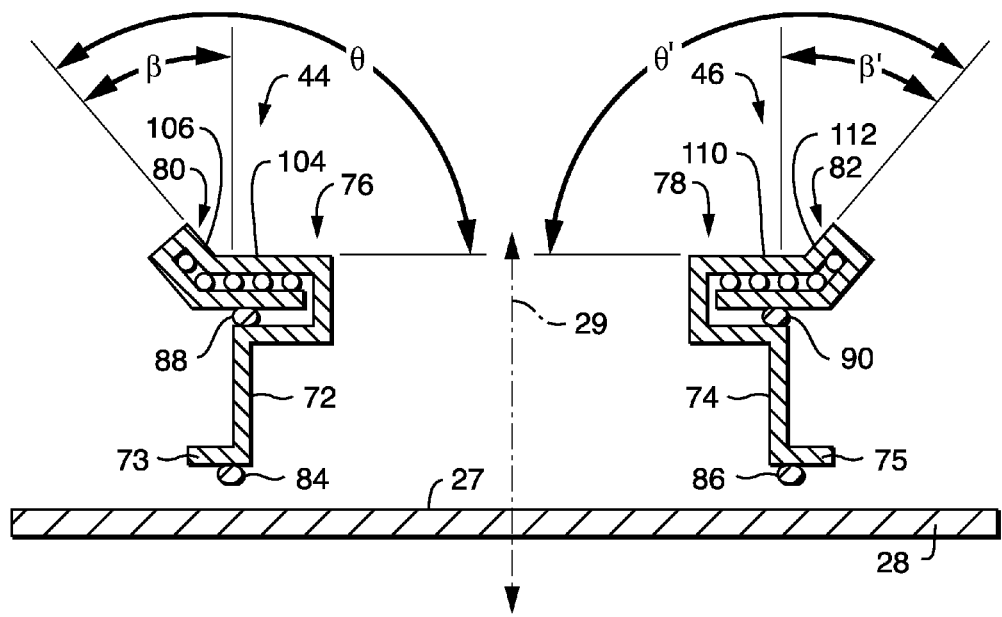
FIG. 23 is a cross-section, exploded view of a crotch region of the absorbent article having the packaging fold lines of FIG. 22 when the absorbent article is in a relaxed, unfolded condition.
Figure 24:
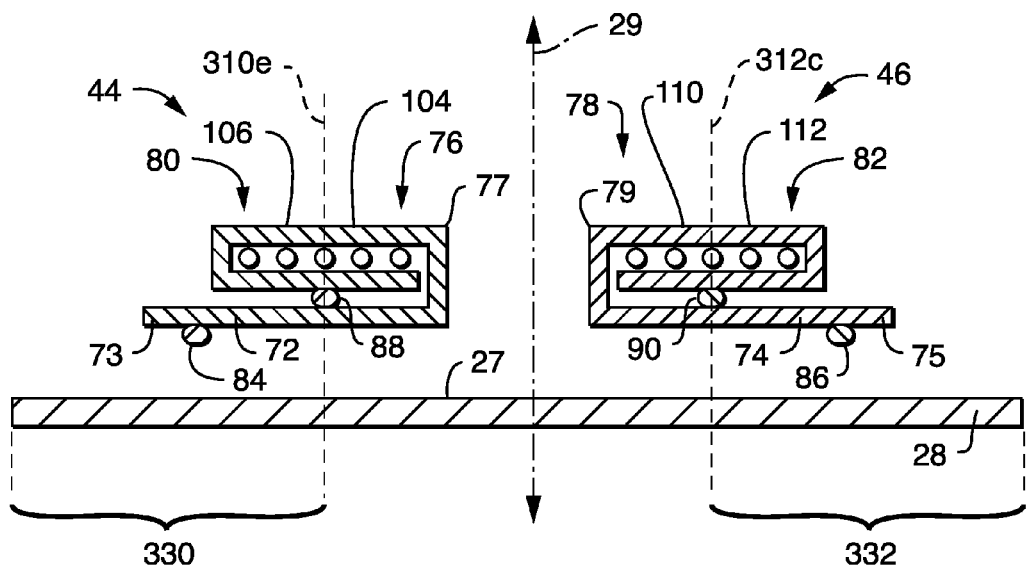
FIG. 24 is a cross-section, exploded view of the body facing liner and containment flaps in the crotch region of the absorbent article of FIG. 1 in a stretched, laid flat condition and illustrating alternative packaging fold lines.

FIGS. 20-25 illustrate alternative packaging fold lines 310c, 310d, 310e, 312c, 312d, 312e for an absorbent article 10 including the containment flaps 44, 46 discussed above. FIGS. 20-25 each show the containment flaps 44, 46 as well as the body facing liner 28 of the absorbent article 10, but omit other features of the absorbent article 10 for purposes of clarity. As shown in FIGS. 20, 22, and 24, when the absorbent article is in the stretched condition prior to folding, the stems 72, 74 of the containment flaps 44, 46 extend substantially parallel to the body facing liner 28. Additionally, the inner flap projections 76, 78 extend substantially parallel to the stems 72, 74, towards the longitudinal axis 29 and the outer flap projections 80, 82 extend substantially parallel to the stems 72, 74 away from the longitudinal axis 29 when the absorbent article 10 is in the stretched condition prior to folding. Each pair of fold lines 310c and 312c, 310d and 312d, and 310e and 312e are positioned such that the fold lines 310c and 312c, 310d and 312d, and 310e and 312e can extend through the upper surface 106 of the inner flap projection 76 and/or the upper surface 110 of the outer flap projection 80 of the containment flap 44 and/or the upper surface 110 of the inner flap projection 78 and/or the upper surface 112 of the outer flap projection 82 of the containment flap 46. By folding the absorbent article 10 and the containment flaps 44, 46 in this manner for packaging purposes, the containment flaps 44, 46 can be kept in an intended position for the period of time that the absorbent article 10 is kept in the packaging. When a user or wearer removes the absorbent article 10 from the packaging, unfolds the absorbent article 10 and places it in the relaxed condition such that the elastic in the absorbent article 10 will gather, the containment flaps 44, 46 can have a tendency to retain some effects from the fold lines 310c and 312c, 310d and 312d, and 310e and 312e that can provide a difference in shape of the containment flaps 44, 46 as compared to the containment flaps 44, 46 when no fold lines extend through the inner flap projections 76, 78 or the outer flap projections 80, 82 of the containment flaps 44, 46. In some circumstances, this controlled shape deformation of the containment flaps 44, 46 can be desirable to help provide beneficial gasketing properties.

FIGS. 20 and 21 illustrate packaging fold lines 310c, 312c extending through the absorbent article 10 including containment flaps 44, 46. The fold lines 310c and 312c can each extend substantially parallel to the longitudinal axis 29 from a front end edge 22 to a rear end edge 24 of the absorbent article 10, just as fold lines 310a, 310b, 312a, and 312b were discussed above. The fold line 310c can be on an opposite side of the longitudinal axis 29 as the fold line 312c. As shown in FIG. 20, the fold line 310c extends through the containment flap 44 at approximately the intersection between the stem 72, the inner flap projection 76, and the outer flap projection 80 of the containment flap 44. Similarly, the fold line 312c extends through the containment flap 46 at approximately the intersection between the stem 74, the inner flap projection 78, and the outer flap projection 82 of the containment flap 46 when the absorbent article 10 is in a stretched and unfolded condition. Because fold lines 310c, 312c extend substantially through the containment flaps 44, 46 at such an intersection point between the inner flap projections 76, 78 and the outer flap projections 80, 82, respectively, for purposes herein, it can be considered that the fold lines 310c, 312c each extend through at least a portion of their respective inner flap projection 76, 78 as well as their respective outer flap projections 80, 82.

The absorbent article 10 can be folded along lines 310c and 312c by folding a longitudinal portion 322 of the absorbent article 10 laterally outside of the folding line 310c towards the longitudinal axis 29 and on top of the body facing surface 27 of the body facing liner 28 and folding a longitudinal portion 324 of the absorbent article 10 laterally outside of the folding line 312c towards the longitudinal axis 29 and on top of the body facing surface 27 of the body facing liner 28.

FIG. 21 illustrates the shape the containment flaps 44, 46 can take after the absorbent article 10 is unfolded from the folding lines 310c, 312c as shown in FIG. 20 and when the absorbent article 10 is in a relaxed condition. As depicted in FIG. 21, the upper surface 104 of the inner flap projection 76 and the upper surface 106 of the outer flap projection 80 of the containment flap 44 can be not parallel to one another as in other embodiments discussed above. Instead, the inner flap projection 76 can extend away from the stem 72 in an upward fashion relative to the body facing liner 28 and the outer flap projection 80 can extend away from the stem 72 in an upward fashion relative to the body facing liner 28 such that the stem 72, the inner flap projection 76, and the outer flap projection 80 form a "Y-shape." More particularly, the upper surface 104 of the inner flap projection 76 can form an angle $\alpha$ with the stem 72 and the upper surface 106 of the outer flap projection 80 can form an angle $\beta$ with the stem 72, with angle $\alpha$ and angle $\beta$ not being equal to 90° in this embodiment. The angle $\alpha$ can be equal to or substantially similar to $\beta$ as shown in FIG. 21, but need not be. As a non-limiting example, the angle $\alpha$ can be from about 5° to about 85°, more preferably from about 15° to about 75°, and even more preferably from about 30° to about 60°. As a non-limiting example, the angle $\beta$ can be from about 5° to about 85°, more preferably from about 15° to about 75°, and even more preferably from about 30° to about 60°. Of course, other values for the angle $\alpha$ and the angle $\beta$ are within the scope of this disclosure.

Similarly, the upper surface 110 of the inner flap projection 78 and the upper surface 112 of the outer flap projection 82 of the containment flap 46 are not parallel to one another as in other embodiments discussed above. As shown in FIG. 21, the inner flap projection 78 can extend away from the stem 74 in an upward fashion relative to the body facing liner 28 and the outer flap projection 82 can extend away from the stem 74 in an upward fashion relative to the body facing liner 28 such that the stem 74, the inner flap projection 78, and the outer flap projection 82 form a "Y-shape." Additionally, the upper surface 110 of the inner flap projection 78 forms an angle $\alpha'$ with the stem 74 and the upper surface 112 of the outer flap projection 82 forms an angle $\beta'$ with the stem 74, with angle $\alpha'$ and angle $\beta'$ not being equal to 90° in this embodiment. The angle $\alpha'$ can be equal or substantially similar to the angle $\beta'$, but need not be. As a non-limiting example, the angle $\alpha'$ can be from about 5° to about 85°, more preferably from about 15° to about 75°, and even more preferably from about 30° to about 60°. As a non-limiting example, the angle $\beta'$ can be from about 5° to about 85°, more preferably from about 15° to about 75°, and even more preferably from about 30° to about 60°. Of course, other values for the angle $\alpha'$ and the angle $\beta'$ are within the scope of this disclosure. Although it is preferred if the angle $\alpha$ is substantially equal to $\alpha'$, such need not be the case. Similarly, although is preferred if the angle $\beta$ is substantially equal to $\beta'$, such need not be the case.

Although the fold lines 310c, 312c extend through the stems 72, 74, respectively, and may create a tendency for the stems 72, 74 to retain such fold lines 310c, 312c, such tendency is minimized by the elasticized nature of the inner flap projections 76, 78, and the outer flap projections 80, 82, that cause the stems 72, 74 to extend away from the body facing liner 28 when the absorbent article 10 in the relaxed condition.

Such a controlled shape of the containment flaps 44, 46 can provide increased gasketing properties in certain circumstances. For example, the "Y-shape" formed by the inner flap projections 76, 78 and the outer flap projections 80, 82 of the containment flaps 44, 46 can adapt to a wearer's skin by flexing as needed. Although the inner flap projections 76, 78 and the outer flap projections 80, 82 can flex to adapt to a wearer's skin, they may still provide some residual force against the wearer's skin to return to their position and shape as shown in FIG. 21, providing an enhanced sealing force against the wearer's skin. This could be especially beneficial in absorbent articles 10 directed towards larger children or adults.

Furthermore, the securing of at least a portion of the inner flap projections 76, 78 and/or the outer flap projections 80, 82 of the containment flaps 44, 46, respectively, in the front end region 12 and/or the rear end region 14 as previously discussed can also provide additional benefits for the embodiment shown in FIGS. 20 and 21. For example, securing at least a portion of the inner flap projections 76, 78 and/or the outer flap projections 80, 82 of the containment flaps 44, 46, respectively, in the front end region 12 and/or the rear end region 14, can help maintain some degree of separation between the inner flap projection 76 with the outer flap projection 80 for the containment flap 44 and some degree of separation between the inner flap projection 78 and the outer flap projection 82 for the containment flap 46. This may help to prevent the inner flap projections 76, 78 from folding completely against the outer flap projections 80, 82, respectively, or vice versa, either before, during, or after application of the absorbent article 10 to the wearer, which may not be desirable. However, it is within the scope of this disclosure that the inner flap projections 76, 78 and/or the outer flap projections 80, 82 of the containment flaps 44, 46 need not be secured in at least a portion of the front end region 12 and/or the rear end region 14.

Turning now to FIGS. 22 and 23, fold lines 310d and 312d are shown extending through containment flaps 44, 46. Fold lines 310d and 312d can each extend substantially parallel to the longitudinal axis 29 from a front end edge 22 to a rear end edge 24 of the absorbent article 10, just as fold lines 310a, 310b, 310c, 312a, 312b, and 312c were discussed above. The fold line 310d can extend through the containment flap 44 through the outer flap projection 80. Similarly, the fold line 312d can extend through the containment flap 46 through the outer flap projection 82. The fold line 310d can be on an opposite side of the longitudinal axis 29 as the fold line 312d.

The absorbent article 10 can be folded along lines 310d and 312d by folding a longitudinal portion 326 of the absorbent article 10 laterally outside of the folding line 310d towards the longitudinal axis 29 and on top of the body facing surface 27 of the body facing liner 28 and folding a longitudinal portion 328 of the absorbent article 10 laterally outside of the folding line 312d towards the longitudinal axis 29 and on top of the body facing surface 27 of the body facing liner 28.

FIG. 23 illustrates the shape the containment flaps 44, 46 can take after the absorbent article 10 is unfolded from the folding lines 310d, 312d as shown in FIG. 22 and when the absorbent article 10 is in a relaxed condition. As illustrated in FIG. 23, the upper surface 106 of the outer flap projection 80 of the containment flap 44 can form an angle $\theta$ with the upper surface 104 of the inner flap projection 76, such that the upper surface 106 of the outer flap projection 80 is not parallel to the upper surface 104 of the inner flap projection 76, as discussed in other embodiments. As a non-limiting example, the angle $\theta$ can be from about 90° to about 175°, more preferably from about 110° to about 165°, and even more preferably from about 120° to about 155°. The outer flap projection 80 can extend away from the stem 72 in an upward fashion relative to the body facing liner 28. Additionally, the upper surface 106 of the outer flap projection 80 can form an angle $\beta$ with the stem 72 not being equal to 90° in this embodiment. As a non-limiting example, the angle $\beta$ can be from about 0° to about 85°, more preferably from about 10° to about 75°, and even more preferably from about 30° to about 60°. Of course, other values for the angle $\theta$ and the angle $\beta$ are within the scope of this disclosure.

Similarly, the upper surface 112 of the outer flap projection 82 of the containment flap 46 can form an angle $\theta'$ with the upper surface 110 of the inner flap projection 78, such that the upper surface 112 of the outer flap projection 82 is not parallel to the upper surface 110 of the inner flap projection 78, as discussed in other embodiments. As a non-limiting example, the angle $\theta'$ can be from about 90° to about 175°, more preferably from about 110° to about 165°, and even more preferably from about 120° to about 155°. As shown in FIG. 23, the outer flap projection 82 can extend away from the stem 74 in an upward fashion relative to the body facing liner 28. Additionally, the upper surface 112 of the outer flap projection 82 forms an angle $\beta'$ with the stem 74 not being equal to 90° in this embodiment. As a non-limiting example, the angle $\beta'$ can be from about 0° to about 85°, more preferably from about 10° to about 75°, and even more preferably from about 30° to about 60°. Of course, other values for the angle $\theta'$ and the angle $\beta'$ are within the scope of this disclosure. Although it is preferred if the angle $\theta$ is substantially equal to $\theta'$, such need not be the case.

Similarly, although is preferred if the angle β is substantially equal to β', such need not be the case.

As noted above with respect to fold lines 310c and 312c, although the fold lines 310d, 312d extend through the stems 72, 74, respectively, and may create a tendency for the stems 72, 74 to retain such a fold line 310d, 312d, such tendency is minimized by the elasticized nature of the inner flap projections 76, 78, and the outer flap projections 80, 82, that cause the stems 72, 74 to extend away from the body facing liner 28 when the absorbent article 10 in the relaxed condition.

A controlled shape having the outer flap projections 80, 82 of the containment flaps 44, 46, respectively, extend away from the stems 72, 74 and upwards in relation to the body facing liner 28 can provide beneficial gasketing properties. Depending on the spacing of the containment flaps 44, 46 from one another and the anatomy of the wearer, the angled nature of the outer flap projections 80, 82 may more closely mimic the wearer's skin profile. Additionally, if the outer flap projections 80, 82 flex to adapt to the wearer's skin, they can provide some residual force against the wearer's skin to return to their position and shape as shown in FIG. 23, providing an enhanced sealing force against the wearer's skin at the outermost point of lateral containment for the containment flaps 44, 46.

Although the fold lines 310d, 312d are depicted in FIG. 22 as extending through a specific portion of the outer flap projections 80, 82, the fold lines 310d, 312d could be positioned closer to the distal edges 81, 83 of the outer flap projections 80, 82, respectively, or closer to the adhesives 88, 90, respectively, that define the intersection between the inner flap projections 76, 78 and the outer flap projections 80, 82, as desired.

The securing of at least a portion of the inner flap projections 76, 78 and/or the outer flap projections 80, 82 of the containment flaps 44, 46, respectively, in the front end region 12 and/or the rear end region 14 as previously discussed can also provide additional benefits for the embodiment shown in FIGS. 22 and 23. For example, securing at least a portion of the inner flap projections 76, 78 and/or the outer flap projections 80, 82 of the containment flaps 44, 46, respectively, in the front end region 12 and/or the rear end region 14, can help maintain the inner flap projections 76, 78 be substantially perpendicular to the stems 72, 74, respectively. It can also help maintain desirable angles β and β' in the crotch region 16 and prevent the outer flap projections 80, 82 from folding completely on top of the inner flap projections 76, 78 respectively, or vice versa, either before, during, or after application of the absorbent article 10 to the wearer, which may not be desirable. However, it is within the scope of this disclosure that the inner flap projections 76, 78 and/or the outer flap projections 80, 82 of the containment flaps 44, 46 need not be secured in at least a portion of the front end region 12 and/or the rear end region 14.

Figure 25:
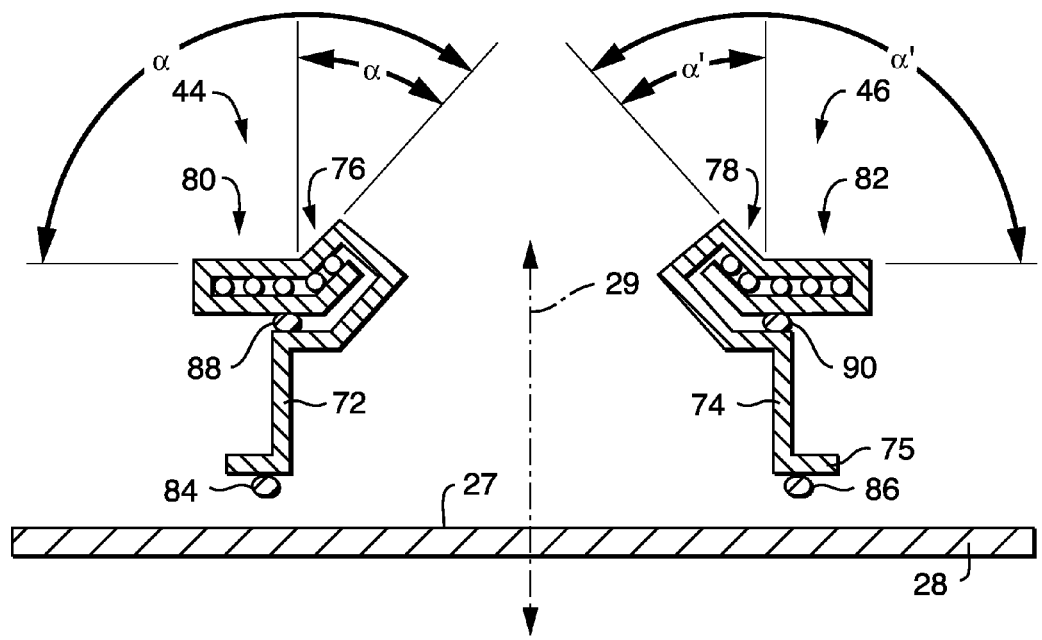
FIG. 25 is a cross-section, exploded view of a crotch region of the absorbent article having the packaging fold lines of FIG. 24 when the absorbent article is in a relaxed, unfolded condition.

FIGS. 24 and 25 illustrate yet another alternative location for packaging fold lines 310e, 312e in the absorbent article 10. The fold lines 310e and 312e are shown extending through containment flaps 44, 46. Fold lines 310e and 312e can each extend substantially parallel to the longitudinal axis 29 from a front end edge 22 to a rear end edge 24 of the absorbent article 10, as fold lines 310a, 310b, 312a, 312b, 310c, 312c, 310d, and 312d discussed above. The fold line 310e can extend through the containment flap 44 through the inner flap projection 76. Similarly, the fold line 312e can extend through the containment flap 46 through the inner flap projection 78. The fold line 310e can be on an opposite side of the longitudinal axis 29 as the fold line 312e.

The absorbent article 10 can be folded along lines 310e and 312e by folding a longitudinal portion 330 of the absorbent article 10 laterally outside of the folding line 310e towards the longitudinal axis 29 and on top of the body facing surface 27 of the body facing liner 28 and folding a longitudinal portion 332 of the absorbent article 10 laterally outside of the folding line 312e towards the longitudinal axis 29 and on top of the body facing surface 27 of the body facing liner 28.

FIG. 25 provides an exemplary illustration of the shape the containment flaps 44, 46 can take after the absorbent article 10 is unfolded from the folding lines 310e, 312e as shown in FIG. 24 and when the absorbent article 10 is in a relaxed condition. The upper surface 104 of the inner flap projection 76 can extend away from the stem 72 in an upward fashion relative to the body facing liner 28 and can form an angle γ with the upper surface 106 of the outer flap projection 80, such that the upper surface 104 of the inner flap projection 76 is not parallel to the upper surface 106 of the outer flap projection 80, as described in other embodiments discussed above. As a non-limiting example, the angle γ can be from about 90° to about 175°, more preferably from about 110° to about 165°, and even more preferably from about 120° to about 155°. Additionally, the upper surface 104 of the inner flap projection 76 can form an angle α with the stem 72 not being equal to 90° in this embodiment. As a non-limiting example, the angle α can be from about 0° to about 85°, more preferably from about 10° to about 75°, and even more preferably from about 30° to about 60°. Of course, other values for the angle γ and the angle α are within the scope of this disclosure.

The upper surface 110 of the inner flap projection 78 can extend away from the stem 74 in an upward fashion relative to the body facing liner 28 and can form an angle γ' with the upper surface 112 of the outer flap projection 82, such that the upper surface 110 of the inner flap projection 78 is not parallel to the upper surface 112 of the outer flap projection 82, as described in other embodiments discussed above. As a non-limiting example, the angle γ' can be from about 90° to about 175°, more preferably from about 110° to about 165°, and even more preferably from about 120° to about 155°. Additionally, the upper surface 110 of the inner flap projection 78 can form an angle α' with the stem 72 not being equal to 90° in this embodiment. As a non-limiting example, the angle α can be from about 0° to about 85°, more preferably from about 10° to about 75°, and even more preferably from about 30° to about 60°. Of course, other values for the angle γ' and the angle α' are within the scope of this disclosure. Although it is preferred if the angle γ is substantially equal to γ', such need not be the case. Similarly, although is preferred if the angle α is substantially equal to α', such need not be the case.

As noted above with respect to fold lines 310c, 312c, 310d, and 312d, although the fold lines 310e, 312e extend through the stems 72, 74, respectively, and may create a tendency for the stems 72, 74 to retain such a fold line 310e, 312e, such tendency is minimized by the elasticized nature of the inner flap projections 76, 78, and the outer flap projections 80, 82, that cause the stems 72, 74 to extend away from the body facing liner 28 when the absorbent article 10 in the relaxed condition.

A controlled shape having the inner flap projections 76, 78 of the containment flaps 44, 46, respectively, extend away from the stems 72, 74 and upwards in relation to the body-facing liner 28 can provide beneficial gasketing properties. Depending on the spacing of the containment flaps 44, 46 from one another and the anatomy of the wearer, the angled nature of the inner flap projections 76, 78 may more closely mimic the wearer's skin profile. Additionally, if the inner flap projections 76, 78 flex to adapt to the wearer's skin, they can provide some residual force against the wearer's skin to return to their position and shape as shown in FIG. 25, providing an enhanced sealing force against the wearer's skin at the innermost point of lateral containment for the containment flaps 44, 46.

Although the fold lines 310e, 312e are depicted in FIG. 24 as extending through a specific portion of the inner flap projections 76, 78, the fold lines 310e, 312e could be positioned closer to the distal edges 77, 79 of the inner flap projections 76, 78, respectively, or closer to the adhesives 88, 90, respectively that define the intersection between the inner flap projections 76, 78 and the outer flap projections 80, 82, as desired.

The securing of at least a portion of the inner flap projections 76, 78 and/or the outer flap projections 80, 82 of the containment flaps 44, 46, respectively, in the front end region 12 and/or the rear end region 14 as previously discussed can also provide additional benefits for the embodiment shown in FIGS. 24 and 25. For example, securing at least a portion of the inner flap projections 76, 78 and/or the outer flap projections 80, 82 of the containment flaps 44, 46, respectively, in the front end region 12 and/or the rear end region 14, can help maintain the outer flap projections 80, 82 be substantially perpendicular to the stems 72, 74, respectively. It can also help maintain desirable angles α and α' in the crotch region 16 and prevent the outer flap projections 80, 82 from folding completely on top of the inner flap projections 76, 78, respectively, or vice versa, either before, during, or after application of the absorbent article 10 to the wearer, which may not be desirable. However, it is within the scope of this disclosure that the inner flap projections 76, 78 and/or the outer flap projections 80, 82 of the containment flaps 44, 46 need not be secured in at least a portion of the front end region 12 and/or the rear end region 14.

Although it may be preferred in some circumstances to have symmetrical containment flaps 44, 46 and/or symmetrical packaging fold lines in the absorbent article 10, it is also within the scope of this disclosure that an absorbent article 10 can include non-symmetrical containment flaps 44, 46 and/or non-symmetrical packaging fold lines. For example, an absorbent article 10 could include one of the packaging fold lines 310a or 310b illustrated in FIGS. 18-19 or one of the packaging fold lines 310c, 310d, or 310e illustrated in FIGS. 20-25 along with any packaging fold line 310a, 310b illustrated in FIGS. 18 and 19 or packaging fold line 312c, 312d, or 312e illustrated in FIGS. 20-25 in any combination that was not described above. As merely one example, an absorbent article 10 could include packaging fold line 310d illustrated in FIGS. 22 and 23 and packaging fold line 310e illustrated in FIGS. 24 and 25, achieving the individual benefits for each containment flap noted above. Depending on the size, shape, and other features of the absorbent article 10 and the intended size of the folded absorbent article 10, one or more of these non-symmetric packaging fold lines combinations can be desirable.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a longitudinal axis and a lateral axis;
    a front end region, a rear end region, a crotch region, the crotch region being disposed between the front end region and the rear end region;
    a front end edge in the front end region, a rear end edge in the rear end region, a first longitudinal side edge and a second longitudinal side edge, the first longitudinal side edge and the second longitudinal side edge each extending from the front end edge to the rear end edge;
    a body facing liner comprising a body facing surface and a garment facing surface;
    a backsheet coupled to the body facing liner;
    an absorbent body positioned between the body facing liner and the backsheet;
    a first containment flap and a second containment flap, the first containment flap and the second containment flap each extending from the front end region to the rear end region, the first containment flap being on a first side of the longitudinal axis, the second containment flap being on a second side of the longitudinal axis, the first containment flap and the second containment flap each comprising:
        a stem bonded to one of the body facing liner and the backsheet, the stem configured to extend away from the body facing surface of the body facing liner and the backsheet in at least the crotch region when the absorbent article is in a relaxed condition;
        an inner flap projection extending laterally from the stem towards the longitudinal axis when the absorbent article is in the relaxed condition, at least a portion of the inner flap projection being elasticized; and
        an outer flap projection, the outer flap projection extending laterally from the stem away from the longitudinal axis and the inner flap projection to a distal end when the absorbent article is in the relaxed condition, at least a portion of the outer flap projection being elasticized,
    a first fold line of the absorbent article for packaging being substantially parallel to the longitudinal axis on the first side of the longitudinal axis and extending from the front end edge to the rear end edge;
    a second fold line of the absorbent article for packaging being substantially parallel to the longitudinal axis on the second side of the longitudinal axis and extending from the front end edge to the rear end edge; and
    wherein the distal end of the outer flap projection of the first containment flap is positioned laterally inside of the first folding line when the absorbent article is in an unfolded and stretched condition.

2. The absorbent article of claim 1, wherein the distal end of the outer flap projection of the second containment flap is positioned laterally inside of the second folding line when the absorbent article is in the unfolded and stretched condition.

3. The absorbent article of claim 2, wherein the stem of the first containment flap is laterally inside of the first folding line and the stem of the second containment flap is laterally inside of the second folding line.

4. The absorbent article of claim 1, wherein the stem of the first containment flap and the stem of the second containment flap are bonded to the body facing liner.

5. The absorbent article of claim 1, wherein the outer flap projection of the first containment flap and the outer flap projection of the second containment flap are each secured in at least a portion of the rear end region and at least a portion of the front end region.

6. The absorbent article of claim 5, wherein the outer flap projection of the first containment flap is bonded to the stem of the first containment flap in the at least a portion of the rear end region and the at least a portion of the front end region and the outer flap projection of the second containment flap is bonded to the stem of the second containment flap in the at least a portion of the rear end region and the at least a portion of the front end region.

7. The absorbent article of claim 6, wherein the inner flap projection of the first containment flap and the inner flap projection of the second containment flap are each secured in at least a portion of the front end region and at least a portion of the rear end region.

8. An absorbent article comprising:
a longitudinal axis and a lateral axis;
a front end region, a rear end region, a crotch region, the crotch region being disposed between the front end region and the rear end region;
a front end edge in the front end region, a rear end edge in the rear end region, a first longitudinal side edge and a second longitudinal side edge, the first longitudinal side edge and the second longitudinal side edge each extending from the front end edge to the rear end edge;
a body facing liner comprising a body facing surface and a garment facing surface;
a backsheet coupled to the body facing liner;
an absorbent body positioned between the body facing liner and the backsheet;
a first containment flap and a second containment flap, the first containment flap and the second containment flap each extending from the front end region to the rear end region, the first containment flap being on a first side of the longitudinal axis, the second containment flap being on a second side of the longitudinal axis, the first containment flap and the second containment flap each comprising:
  a stem bonded to one of the body facing liner and the backsheet, the stem configured to extend away from the body facing surface of the body facing liner and the backsheet in at least the crotch region when the absorbent article is in a relaxed condition, the stem of the first containment flap being positioned laterally inward of the first longitudinal side edge and the stem of the second containment flap being positioned laterally inward of the second longitudinal side edge;
  an inner flap projection extending laterally from the stem towards the longitudinal axis to a distal end when the absorbent article is in the partially relaxed state, at least a portion of the inner flap projection being elasticized; and
  an outer flap projection, the outer flap projection extending laterally from the stem away from the longitudinal axis and the inner flap projection when the absorbent article is in the relaxed condition, at least a portion of the outer flap projection being elasticized,
a first fold line of the absorbent article for packaging being substantially parallel to the longitudinal axis on the first side of the longitudinal axis and extending from the front end edge to the rear end edge;
a second fold line of the absorbent article for packaging being substantially parallel to the longitudinal axis on the second side of the longitudinal axis and extending from the front end edge to the rear end edge;
wherein the distal end of the inner flap projection of the first containment flap is positioned laterally outside of the first folding line when the absorbent article is in an unfolded and stretched condition, and
wherein the first fold line extends through at least a portion of the absorbent body.

9. The absorbent article of claim 8, wherein the distal end of the inner flap projection of the second containment flap is positioned laterally outside of the second folding line when the absorbent article is in the unfolded and stretched condition.

10. The absorbent article of claim 9, wherein the stem of the first containment flap is laterally outside of the first folding line and the stem of the second containment flap is laterally outside of the second folding line.

11. The absorbent article of claim 8, further comprising:
a first elasticized leg cuff and a second elasticized leg cuff, the first elasticized leg cuff being positioned on the first side of the longitudinal axis and laterally outward from the stem of the first containment flap, the second elasticized leg cuff being positioned on the second side of the longitudinal axis and laterally outward from the stem of the second containment flap.

12. The absorbent article of claim 8, wherein the outer flap projection of the first containment flap and the outer flap projection of the second containment flap are each secured in at least a portion of the rear end region and at least a portion of the front end region.

13. The absorbent article of claim 12, wherein the outer flap projection of the first containment flap is bonded to the stem of the first containment flap in the at least a portion of the rear end region and the at least a portion of the front end region and the outer flap projection of the second containment flap is bonded to the stem of the second containment flap in the at least a portion of the rear end region and the at least a portion of the front end region.

14. The absorbent article of claim 12, further comprising a waist elastic coupled to the body facing liner and the first and the second containment flap in the rear end region; the waist elastic including a body facing surface and a garment facing surface, the garment facing surface of the waist elastic being bonded to the outer flap projection to secure the outer flap projection of the first containment flap in the at least a portion of the rear end region and to secure the outer flap projection of the second containment flap in the at least a portion of the rear end region.

15. The absorbent article of claim 12, wherein the inner flap projection of the first containment flap and the inner flap projection of the second containment flap are each secured in at least a portion of the front end region and at least a portion of the rear end region.

16. An absorbent article comprising:
a longitudinal axis and a lateral axis;
a front end region, a rear end region, a crotch region, the crotch region being disposed between the front end region and the rear end region;

a front end edge in the front end region, a rear end edge in the rear end region, a first longitudinal side edge and a second longitudinal side edge, the first longitudinal side edge and the second longitudinal side edge each extending from the front end edge to the rear end edge;

a body facing liner comprising a body facing surface and a garment facing surface;

a backsheet coupled to the body facing liner;

an absorbent body positioned between the body facing liner and the backsheet;

a first containment flap and a second containment flap, the first containment flap and the second containment flap each extending from the front end region to the rear end region, the first containment flap being on a first side of the longitudinal axis, the second containment flap being on a second side of the longitudinal axis, the first containment flap and the second containment flap each comprising:

a stem bonded to one of the body facing liner and the backsheet, the stem configured to extend away from the body facing surface of the body facing liner and the backsheet in at least the crotch region when the absorbent article is in a relaxed condition and extend substantially parallel to the body facing surface of the body facing liner and the backsheet when the absorbent article is in a stretched condition;

an inner flap projection extending laterally from the stem towards the longitudinal axis when the absorbent article is in the relaxed condition, the inner flap projection extending substantially parallel to the stem towards the longitudinal axis when the absorbent article is in the stretched condition, at least a portion of the inner flap projection being elasticized; and an outer flap projection, the outer flap projection extending laterally from the stem away from the longitudinal axis and the inner flap projection to a distal end when the absorbent article is in the relaxed condition, the outer flap projection extending substantially parallel to the stem away from the longitudinal axis when the absorbent article is in the stretched condition, at least a portion of the inner flap projection being elasticized;

a first fold line of the absorbent article for packaging being substantially parallel to the longitudinal axis on the first side of the longitudinal axis and extending from the front end edge to the rear end edge and through at least a portion of the first containment flap including through at least one of the inner flap projection of the first containment flap and the outer flap projection of the first containment flap when the absorbent article is in an unfolded and stretched condition; and a second fold line of the absorbent article for packaging being substantially parallel to the longitudinal axis on the second side of the longitudinal axis and extending from the front end edge to the rear end edge.

17. The absorbent article of claim 16, wherein the second fold line extends through at least a portion of the second containment flap including at least one of the inner flap projection of the second containment flap and the outer flap projection of the second containment flap when the absorbent article is in the unfolded and stretched condition.

18. The absorbent article of claim 16, wherein the first fold line extends through the at least a portion of the first containment flap at about an intersection between the stem, the inner flap projection, and the outer flap projection of the first containment flap.

19. The absorbent article of claim 18, wherein the second fold line extends through the second containment flap at about an intersection between the stem, the inner flap projection, and the outer flap projection of the second containment flap when the absorbent article is in the unfolded and stretched condition.

20. The absorbent article of claim 16, wherein the first fold line extends through the outer flap projection of the first containment flap.

21. The absorbent article of claim 20, wherein the second fold line extends through the outer flap projection of the second containment flap when the absorbent article is in the unfolded and stretched condition.

22. The absorbent article of claim 16, wherein the first fold line extends through the inner flap projection of the first containment flap.

23. The absorbent article of claim 22, wherein the second fold line extends through the inner flap projection of the second containment flap when the absorbent article is in the unfolded and stretched condition.

24. The absorbent article of claim 16, wherein the first fold line extends through the at least a portion of the first containment flap such that a top surface of the outer flap projection of the first containment flap is not parallel to a top surface of the inner flap projection of the first containment flap when the absorbent article is in the relaxed condition.

25. The absorbent article of claim 24, wherein the second fold line extends through the at least a portion of the second containment flap when the absorbent article is in the unfolded and stretched condition such that a top surface of the outer flap projection of the second containment flap is not parallel to a top surface of the inner flap projection of the second containment flap when the absorbent article is in the relaxed condition.

26. The absorbent article of claim 16, wherein the first fold line extends through the at least a portion of the first containment flap such that the inner flap projection of the first containment flap extends away from the stem of the first containment flap and upwards from the body facing liner and the outer flap projection of the first containment flap extends away from the stem of the first containment flap and upwards from the body facing liner when the absorbent article is in an unfolded and relaxed condition, and wherein the second fold line extends through the at least a portion of the second containment flap when the absorbent article is in the unfolded and stretched condition such that the inner flap projection of the second containment flap extends away from the stem of the second containment flap and upwards from the body facing liner and the outer flap projection of the second containment flap extends away from the stem of the second containment flap and upwards from the body facing liner when the absorbent article is in the unfolded and relaxed condition.

* * * * *